US010457927B2

(12) United States Patent
Dolly et al.

(10) Patent No.: US 10,457,927 B2
(45) Date of Patent: Oct. 29, 2019

(54) MULTIPROTEASE THERAPEUTICS FOR CHRONIC PAIN

(71) Applicant: Dublin City University, Dublin (IE)

(72) Inventors: James Oliver Dolly, Dublin (IE); Jiafu Wang, Dublin (IE); Jianghui Meng, Dublin (IE)

(73) Assignee: Dublin City University, Dublin (IE)

( * ) Notice: Subject to any disclaimer, the term of this patent is extended or adjusted under 35 U.S.C. 154(b) by 222 days.

(21) Appl. No.: 14/978,478

(22) Filed: Dec. 22, 2015

(65) Prior Publication Data

US 2016/0230159 A1   Aug. 11, 2016

Related U.S. Application Data

(62) Division of application No. 14/244,162, filed on Apr. 3, 2014, now Pat. No. 9,216,210.

(60) Provisional application No. 61/920,053, filed on Dec. 23, 2013.

(51) Int. Cl.
| | | |
|---|---|---|
| *C12N 9/52* | (2006.01) | |
| *A61K 38/48* | (2006.01) | |
| *C07K 14/33* | (2006.01) | |
| *A61K 38/00* | (2006.01) | |

(52) U.S. Cl.
CPC ............ *C12N 9/52* (2013.01); *A61K 38/4893* (2013.01); *C07K 14/33* (2013.01); *C12Y 304/24069* (2013.01); *A61K 38/00* (2013.01); *C07K 2319/00* (2013.01); *C07K 2319/50* (2013.01); *Y02A 50/469* (2018.01)

(58) Field of Classification Search
None
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | |
| 5,714,468 A | 2/1998 | Binder | |
| 5,989,545 A | 11/1999 | Foster et al. | |
| 6,063,768 A | 5/2000 | First | |
| 6,113,915 A | 9/2000 | Aoki et al. | |
| 6,139,845 A | 10/2000 | Donovan | |
| 6,143,306 A | 11/2000 | Donovan | |
| 6,203,794 B1 | 3/2001 | Dolly et al. | |
| 6,265,379 B1 | 7/2001 | Donovan | |
| 6,299,893 B1 | 10/2001 | Schwartz et al. | |
| 6,306,403 B1 | 10/2001 | Donovan | |
| 6,319,505 B1 | 11/2001 | Aoki et al. | |
| 6,337,075 B1 | 1/2002 | Donovan | |
| 6,358,917 B1 | 3/2002 | Carruthers et al. | |
| 6,358,926 B2 | 3/2002 | Donovan | |
| 6,368,605 B1 | 4/2002 | Donovan | |
| 6,395,513 B1 | 5/2002 | Foster et al. | |
| 6,416,765 B1 | 7/2002 | Donovan | |
| 6,423,319 B1 | 7/2002 | Brooks et al. | |
| 6,458,365 B1 | 10/2002 | Aoki et al. | |
| 6,464,986 B1 | 10/2002 | Aoki et al. | |
| 6,565,870 B1 | 5/2003 | Donovan | |
| 6,620,415 B2 | 9/2003 | Donovan | |
| 6,623,742 B2 | 9/2003 | Voet | |
| 6,641,820 B1 | 11/2003 | Donovan | |
| 6,683,049 B1 | 1/2004 | Aoki et al. | |
| 6,740,321 B1 | 5/2004 | Donovan | |
| 6,767,544 B2 | 7/2004 | Brooks et al. | |
| 6,776,990 B2 | 8/2004 | Sachs et al. | |
| 6,776,992 B2 | 8/2004 | Aoki et al. | |
| 6,827,931 B1 | 12/2004 | Donovan | |
| 6,838,434 B2 | 1/2005 | Voet | |
| 6,843,998 B1 | 1/2005 | Steward et al. | |
| 6,869,610 B2 | 3/2005 | Aoki et al. | |
| 6,872,397 B2 | 3/2005 | Aoki et al. | |
| 7,132,259 B1 * | 11/2006 | Dolly .................. C12N 9/52 435/212 |
| 7,208,466 B1 | 4/2007 | Foster et al. | |
| 7,422,877 B2 | 9/2008 | Dolly et al. | |
| 7,514,088 B2 | 4/2009 | Steward et al. | |
| 7,740,868 B2 | 6/2010 | Steward et al. | |
| 7,897,157 B2 | 3/2011 | Steward et al. | |
| 7,959,933 B2 | 6/2011 | Dolly et al. | |
| 7,985,411 B2 | 7/2011 | Dolly et al. | |

(Continued)

FOREIGN PATENT DOCUMENTS

| | | |
|---|---|---|
| WO | 9532738 A1 | 12/1995 |
| WO | 9633273 A1 | 10/1996 |

(Continued)

OTHER PUBLICATIONS

Boddul et al, FEBS Journal, 2014, 281:750-765.*
Dolly et al, In: Engineering of botulinum neurotoxins as novel therapeuticd tools, 2015, pp. 995-1015.*
Rostamian et al, Iranian Biomedical Journal 16 (4): 185-192 (Oct. 2012).*
Dolly et al, Current Opinion in Pharmacology, 2012, 12:100-108.*
Wang et al, Biochem. J., 2012, 444:59-67.*
Valipour et al, World J. Microbiol. Biotechnol., 2014, 30:1861-1867.*
Dolly J Oliver et al: "Novel therapeutics based on recombinant botulinum neurotoxins to normalize the release of transmitters and pain mediators" FEBS Journal, vol. 278, No. 23, Dec. 2011, pp. 4454-4466.

(Continued)

*Primary Examiner* — Nita M. Minnifield
(74) *Attorney, Agent, or Firm* — Carlos A. Fisher; Stout, Uxa & Buyan, LLP

(57) ABSTRACT

The invention includes Clostridial neurotoxin derivatives containing at least two light chain endopeptidase domains, and nucleic acids encoding such Clostridial neurotoxin derivatives. In preferred embodiments, the invention includes methods and compositions for the treatment of inflammatory disorders (such as arthritis); chronic pain, such as neuropathic pain and inflammatory pain through the use of such Clostridial neurotoxin derivatives, including those derived from an intact BoNT/A having an LC/E-derived endopeptidase joined to the LC/A endopeptidase.

20 Claims, 7 Drawing Sheets

Specification includes a Sequence Listing.

(56) References Cited

U.S. PATENT DOCUMENTS

| | | | |
|---|---|---|---|
| 8,052,979 | B2 | 11/2011 | Steward et al. |
| 8,273,358 | B2 | 11/2012 | Steward et al. |
| 8,460,682 | B2 | 6/2013 | Steward et al. |
| 8,623,999 | B2 | 1/2014 | Steward et al. |
| 8,748,151 | B2 | 6/2014 | Frevert |
| 8,894,713 | B2 | 11/2014 | Frevert |
| 9,005,628 | B2 * | 4/2015 | Dolly .................. 424/184.1 |
| 9,447,405 | B2 * | 9/2016 | Johnson .................. C12N 9/96 |
| 10,240,138 | B2 * | 3/2019 | Madec .................. C07K 14/60 |
| 2002/0010138 | A1 | 1/2002 | Aoki et al. |
| 2003/0166238 | A1 | 9/2003 | Shone et al. |
| 2003/0211121 | A1 | 11/2003 | Donovan |
| 2004/0013692 | A1 | 1/2004 | Aoki et al. |
| 2004/0037852 | A1 | 2/2004 | Aoki et al. |
| 2004/0062776 | A1 | 4/2004 | Voet |
| 2004/0086531 | A1 | 5/2004 | Barron |
| 2004/0115139 | A1 | 6/2004 | Katz et al. |
| 2004/0126396 | A1 | 7/2004 | Aoki et al. |
| 2004/0126397 | A1 | 7/2004 | Aoki et al. |
| 2004/0151740 | A1 | 8/2004 | Aoki et al. |
| 2004/0175399 | A1 | 9/2004 | Schiffman |
| 2004/0176299 | A1 | 9/2004 | Sachs et al. |
| 2004/0180061 | A1 | 9/2004 | Donovan |
| 2004/0234532 | A1 | 11/2004 | First |
| 2004/0253274 | A1 | 12/2004 | Voet |
| 2005/0031648 | A1 | 2/2005 | Brin et al. |
| 2005/0169942 | A1 | 8/2005 | Li et al. |
| 2006/0068494 | A1 | 3/2006 | Perreault |
| 2006/0110410 | A1 | 5/2006 | Shone et al. |
| 2006/0211619 | A1 | 9/2006 | Steward et al. |
| 2008/0032931 | A1 * | 2/2008 | Steward .................. C07K 1/22 514/1.2 |
| 2010/0233741 | A1 | 9/2010 | Wang et al. |
| 2011/0189162 | A1 | 8/2011 | Ghanshani et al. |
| 2012/0039941 | A1 | 2/2012 | Barbieri et al. |
| 2014/0099294 | A1 * | 4/2014 | Dolly .................. C12N 9/96 424/94.3 |
| 2014/0255376 | A1 * | 9/2014 | Johnson .................. C12N 9/96 424/94.3 |
| 2015/0174217 | A1 * | 6/2015 | Dolly .................. C07K 14/33 424/94.67 |
| 2016/0230159 | A1 * | 8/2016 | Dolly .................. C07K 14/33 |

FOREIGN PATENT DOCUMENTS

| | | | |
|---|---|---|---|
| WO | 9807864 | A1 | 2/1998 |
| WO | 9917806 | A1 | 4/1999 |
| WO | 9955359 | A1 | 11/1999 |
| WO | 0114570 | A1 | 3/2001 |
| WO | 0240506 | A2 | 5/2002 |
| WO | 0244199 | A2 | 6/2002 |
| WO | 2005035730 | A2 | 4/2005 |
| WO | 2006011966 | A1 | 2/2006 |
| WO | 2006099590 | A2 | 9/2006 |
| WO | 2007138336 | A2 | 12/2007 |
| WO | 2011146704 | A1 | 11/2011 |
| WO | 2014099294 | A1 | 6/2014 |
| WO | WO 2014/113539 | A1 * | 7/2014 |
| WO | WO 2015/097087 | A1 * | 7/2015 |
| WO | WO 2016/180533 | A1 * | 11/2016 |

OTHER PUBLICATIONS

Jiafu Wang et al: "A Dialeucine in the Protease of Botulinum Toxin A underlies Its Long-lived Neuroparalysis Transfer of Longetivity to a Novel Potential Therapeutic", Journal of Biological Chemistry, American Society for Biochemistry and Molecular Biology, US, [Online], vol. 286, No. 8, Feb. 25, 2011, pp. 6375-6385.

J. Wang et al: "Novel Chimeras of Botulinum Neurotoxins A and E Unveil Contributions from the Binding Translocation, and Protease Domains to Their Functional Characteristics", Journal of Biological Chemistry, vol. 283, No. 25, Apr. 17, 2008, pp. 16993-17002.

J. Wang et al: Novel chimeras of botulinum and tetanus neurotoxins yield insights into their distinct sites of neuroparalysis, The FASEB Journal, vol. 1.26. No. 12, Dec. 2012, pp. 5035-5048.

Gary W. Lawrence et al: "Therapeutic effectiveness of botulinum neurotoxin A: Potent blockade of autonomic transmission by targeted cleavage of only the pertinent SNAP-25" Neuropharmacaology, vol. 70, Jul. 1, 2013, pp. 287-295.

International Search Report, PCT/EP2014/078732, dated Dec. 19, 2014.

Allergan, Inc. U.S. Appl. No. 60/662,151, filed Mar. 15, 2005.

Benefield et al. "Molecular assembly of botulinum neurotoxin progenitor complexes", www.pnas.org.

Meng et al. "Activation of TRPV1 Mediates Calcitonin Gene-Related Peptode Release, Which excited Trigimenal Sensory Neurons and is Attenuated by a Retargeted Botulinum Toxin with Anti-Nociceptive Potential" Journal of Neuroscience, Apr. 15, 2009. 19(15) pp. 4981-4992.

Decosterd et al. "Spared nerve injury: an animal model of persistent peripheral neuropathic pain" Pain 87 (2000) pp. 149-158.

Dong et al. "Glycosylated SV2A and SV2B Mediate the Entry of Botulinum E into Neurons" Molecular Biology of the Cell vol. 19, 5226-5237, Dec. 2008.

Rouzer, Carol A. "Anatomy of a Neurotoxin" http://www.vanderbuilt.edu/vicb/DiscoveriesArchives/anatomy_anatomy_of_a_neurotoxin.html.

Naumann et al. "Assesment: Botuminum Neurotoxin in the Treatment of Autonomic Disorders and Pain (An evidence Based Review)" Report of the Therapeutics and Technology Assessment Subcommittee of the American Academy of Nerology, Neurology 70, pp. 1707-1714.

Wang et al. "Longer-acting and highly potent chemaeric inhibitors of excessive exocytosis created with domains from botilinim neurotoxin A and B" Biochem. J.. (2012) 444, pp. 59-67.

Rummel et al. "Exchange of the Hcc domain mediating double receptor recognition improves the pharmacaodynamic properties of botulinum neurotoxin" FEBS Journal 278(2011) pp. 4506-4515.

Lawrence et al. "Excitatory Cholineric and Purnergic Signaling in Bladder are Equally Suceptible to Botulinum Neurotoxin A Consistent with Co-Release of Transmitters form Efferent Fibers" The Journal of Pharmacology and Experimental Therapeutics 334: pp. 1080-1086. (2010).

Chaddock, John "Transforming the Domain Structure of Botulinum Neurotoxins into Novel Therapeutics".

Pickett, Andy "Re-Engineering Clostridal Neurotoxins for the Treatment of Chronic Pain" Current status and Future Prospects. Biodrugs 2010:24(3): 173-182.

Massuyer et al. Annu. Rev. Pharmacol. Toxicol. 2014.54:27-51.

Massuyer et al, Acta Cryst. (2011). F67, 1466-1472.

* cited by examiner

BoNT/E

| LC/E | H_N/E | H_C/E |

S-S (between H_N/E and H_C/E)

BoNT/A

| LC/A | H_N/A | H_C/A |

S-S (between LC/A and H_N/A)

Fusing LC/E to BoNT/A

LC/E-BoNT/A

| LC/E | LC/A | H_N/A | H_C/A |

S-S (between LC/A and H_N/A)

Coomassie Stained | Western Blotting

MW (kDa): 250, 150, 100, 75, 50, 37, 25, 20, 15

SC / DC with DTT (− / +)

Anti-LC/E | Anti-BoNT/A | Anti-His$_6$

← SC/DC
← LC/E-LC/A & H_C/A (Not Resolved)

[BoNT]pM  1000  100  10  1  0.1  0.01  0

Syntaxin 1

SNAP-25
SNAP-25$_A$

BoNT/A

Syntaxin 1

SNAP-25
SNAP-25$_A$
SNAP-25$_E$

LC/E-BoNT/A

FIG. 4

♦ LCE-BoNT/A, 0.5 U
☐ nBoNT/A, 6 U
▼ nBONT/E, 7 U

DAS Value (±SEM: n=10)

Days

FIG. 5

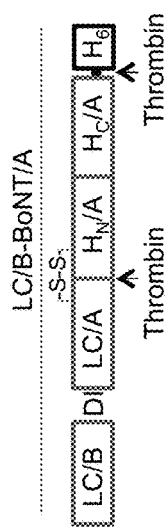
FIG. 8A
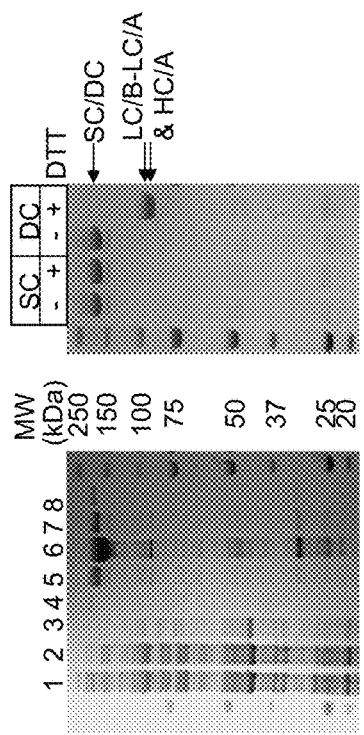
FIG. 8B
FIG. 8C
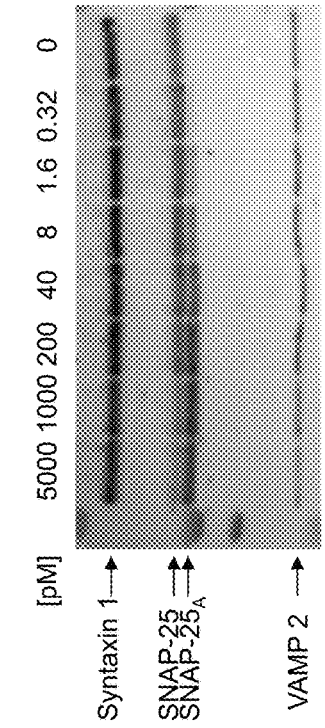
FIG. 8D
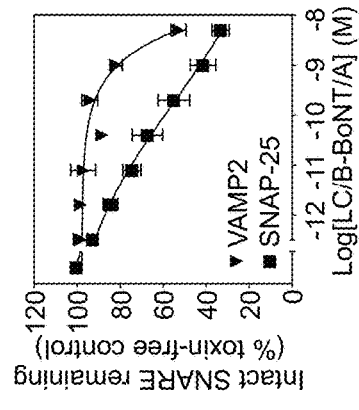
FIG. 8E

LC/D-BoNT/C1: inactivates all three SNARE proteins

| LC/D | D | LC/C1 | H$_N$/C1 | H$_C$/C1 | His$_6$ |

-S-S-

Thrombin (between LC/C1 and H$_N$/C1)
Thrombin (between H$_C$/C1 and His$_6$)

Cleaves VAMP 1-3 → (from LC/D)
Truncates Syntaxin 1-3 and SNAP-25 → (from LC/C1)

FIG. 9

MULTIPROTEASE THERAPEUTICS FOR CHRONIC PAIN

CROSS REFERENCE TO RELATED APPLICATIONS

This application is a divisional of U.S. patent application Ser. No. 14/244,162, filed Apr. 3, 2014 (now U.S. Pat. No. 9,216,210), which claimed priority pursuant to 35 U.S.C. § 119(e) to provisional patent application No. 61/920,053, filed Dec. 23, 2013, each of which is hereby individually incorporated herein by reference in its entirety.

REFERENCE TO A SEQUENCE LISTING

The instant application contains a Sequence Listing which has been submitted in ASCII format via EFS-Web and is hereby incorporated by reference in its entirety. Said ASCII copy, created on Mar. 25, 2014, is named A-05047_SL.txt and is 132,759 bytes in size.

BACKGROUND

The present invention is drawn to methods and composition involving Clostridial neurotoxin derivatives having an enhanced ability to disrupt exocytosis of pain and/or inflammatory mediators from nociceptors or inducers of inflammation, thus preventing pain.

Botulinum neurotoxin (BoNT) serotypes A-G, produced by *Clostridium botulinum*, are the most potent poisons known due to specifically blocking the release of acetylcholine from peripheral nerves by proteolytically cleaving SNARE ("Soluble NSF Attachment Protein Receptors") proteins, which mediate the fusion of the synaptic vesicle with the cell membrane, and are thus essential for $Ca^{2+}$-stimulated exocytosis of neurotransmitters and pain peptides from the neuron.

The ability of Clostridial toxins such as, e.g., Botulinum neurotoxins (BoNTs) (including the BoNT serotypes BoNT/A, BoNT/B, BoNT/C1, BoNT/D, BoNT/E, BoNT/F and BoNT/G, as well as tetanus toxin TeTx) to inhibit neuronal transmission are being exploited in a wide variety of therapeutic and cosmetic applications, see e.g., Ward AB and Barnes MP, Clinical Users of Botulinum Toxins (Cambridge University Press, Cambridge 2007). As an example, the BoNT/A-derived agent BOTOX® has been used in one or more countries for each the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

There are Clostridial toxins other than the *C. botulinum*- and *C. tetanus*-derived toxins; these include, without limitation, the toxins of *C. perfringins, C. septicum, C. difficile, C. spiroforme, C. butyricum* and *C. barati*. However, it will be understood that in this specification a reference to "Clostridial toxins" or a similar reference, concerns the neurotoxins of *C. botulinum* subtypes and *C. tetani* subtypes, unless specifically or contextually indicated otherwise.

In addition, Clostridial toxin therapies are used or have been proposed for treating conditions including, without limitation, a) neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May 7, 2004); and Kei Roger Aoki, et al., Method for Treating Dystonia with Botulinum Toxin C to G, U.S. Pat. No. 6,319,505 (Nov. 20, 2001);

b) eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004);

c) pain, see e.g., Kei Roger Aoki et al., Pain Treatment by Peripheral Administration of a Neurotoxin, U.S. Pat. No. 6,869,610 (Mar. 22, 2005); Stephen Donovan, Clostridial Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, Botulinum Toxin Therapy for Fibromyalgia, U.S. Patent Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004);

d) muscle injuries, see e.g., Gregory F. Brooks, Methods for Treating Muscle Injuries, U.S. Pat. No. 6,423,319 (Jul. 23, 2002);

e) headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998);

f) cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004);

e) neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001);

g) neuropsychiatric disorders, see e.g., Stephen Donovan, Botulinum Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003);

f) endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000);

g) cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005);

h) otic disorders, see e.g., Stephen Donovan, Neurotoxin Therapy for Inner Ear Disorders, U.S. Pat. No. 6,358,926 (Mar. 19, 2002); and Stephen Donovan, Method for Treating Otic Disorders, U.S. Pat. No. 6,265,379 (Jul. 24, 2001);

i) autonomic disorders, see, e.g., Pankai J. Pasricha and Anthony N. Kalloo, Method for Treating Gastrointestinal Muscle Disorders and Other Smooth Muscle Dysfunction, U.S. Pat. No. 5,437,291 (Aug. 1, 1995);

j) as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R. First, Application of Botulinum Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of Botulinum Toxin for Treatment of Downturned Mouth, U.S. Pat. No. 6,358,917 (Mar. 19, 2002); Stephen Donovan, Use of a Clostridial Toxin to Reduce Appetite, U.S. Patent Publication No. 2004/40253274 (Dec. 16, 2004); and Howard I. Katz and Andrew M. Blumenfeld, Botulinum Toxin Dental Therapies and Procedures, U.S. Patent Publication No. 2004/0115139 (Jun. 17, 2004); Kei Roger Aoki, et al., Treatment of Neuromuscular Disorders and Conditions with Different Botulinum, U.S. Patent Publication No. 2002/0010138 (Jan. 24, 2002); and Kei Roger Aoki, et al., Use of Botulinum Toxins for Treating Various Disorders and Conditions and Associated Pain, U.S. Patent Publication No. 2004/0013692 (Jan. 22, 2004).

Table 2, below, provides the amino acid sequences of isotypes of various currently known botulinum-related (BoNT and TeTX) Clostridial toxins. These toxins possess a minimum of approximately 35% amino acid identity with each other and share the same general functional domain organization and overall structural architecture. The naturally-occuring Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment. This post-translational processing yields a mature di-chain molecule comprising an approximately 50 kDa light chain (LC) and an approximately 100 kDa heavy chain (HC) held together by a single inter-chain disulfide bond and noncovalent interactions.

Each mature di-chain Clostridial toxin molecule comprises three functionally distinct domains: 1) an enzymatic domain located in the LC that includes a metalloprotease region containing a zinc-dependent endopeptidase activity which specifically targets one or more SNARE proteins that mediate the fusion of the synaptic vesicle with the cell membrane; 2) a translocation domain contained within the amino-terminal half of the H chain (termed "$H_N$") that facilitates release of at least the LC chain of the toxin from an endosome into the cytoplasm of the target cell; and 3) a binding domain found within the carboxyl-terminal half of the H chain ($H_C$) that determines the binding activity and binding specificity of the toxin.

The $H_C$ comprises $H_{CN}$ and $H_{CC}$ sub-domains (the N- and C-terminal portions of $H_C$, respectively). There is now substantial evidence that most or all BoNT/X toxins bind a target cell using a "dual receptor", wherein the $H_C$ portion of the toxin comprising both $H_{CN}$ and $H_{CC}$ subdomains binds certain cell surface gangliosides and a protein receptor (perhaps glycosylated); binding of the protein receptor facilitates the internalization of the toxin within the cell. By "X" is meant any serotype of botulinum toxin. Although the term "BoNT/X" is generally used to indicate subtypes of botulinum toxin, the term may also include TeTX regions thereof. $H_{CC}$ binds the receptor complex located at the surface of the target cell.

It will be understood that there exist strains or subtypes of each serotype of these toxins; these may vary somewhat in their amino acid sequences, particularly (but not exclusively) in non-critical regions (so called "variable" regions) without a substantial change in the identity or activity characteristic of the indicated toxin or toxin domain.

In Table 1 below, the standard one-letter and three letter amino acid codes are provided:

TABLE 1

| Amino Acid | Three letter code | One letter code |
|---|---|---|
| alanine | Ala | A |
| arginine | Arg | R |
| asparagine | Asn | N |
| aspartic acid | Asp | D |
| asparagine or aspartic acid | Asx | B |
| cysteine | Cys | C |
| glutamic acid | Glu | E |
| glutamine | Gln | Q |
| glutamine or glutamic acid | Glx | Z |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Try | W |
| tyrosine | Tyr | Y |
| valine | Val | V |

TABLE 2

Clostridial Toxin Reference Sequences and Regions
(identified, from amino to carboxy direction;
amino acid number to amino acid number)

| Toxin | SEQ ID NO: | LC | $H_N$ | $H_C$ |
|---|---|---|---|---|
| BoNT/A | 7 | M1-K448 | A449-K871 | N872-L1296 |
| BoNT/B | 8 | M1-K441 | A442-S858 | E859-E1291 |
| BoNT/C 1 | 9 | M1-K449 | T450-N866 | N867-E1291 |
| BoNT/D | 10 | M1-R445 | D446-N862 | S863-E1276 |
| BoNT/E | 11 | M1-R422 | K423-K845 | R846-K1252 |

TABLE 2-continued

Clostridial Toxin Reference Sequences and Regions
(identified, from amino to carboxy direction;
amino acid number to amino acid number)

| Toxin | SEQ ID NO: | LC | $H_N$ | $H_C$ |
|---|---|---|---|---|
| BoNT/F | 12 | M1-K439 | A440-K864 | K865-E1274 |
| BoNT/G | 13 | M1-K446 | S447-S863 | N864-E1297 |
| TeNT | 14 | M1-A457 | S458-V879 | I880-D1315 |

Those of ordinary skill in the art recognize that Clostridial subtype toxin variants may exist in nature, having variations in the amino acid sequences shown above (or in the nucleotide sequences encoding these amino acid sequences). As used herein, the term "naturally-occurring Clostridial domain variant" means any Clostridial domain (endopeptidase, translocation, and/or binding domains) produced by a naturally-occurring process, including, without limitation, Clostridial domain isoforms produced from alternatively-spliced transcripts, Clostridial domain isoforms produced by spontaneous mutations and Clostridial domain subtypes. As used herein, a naturally-occurring Clostridial domain variant functions in substantially the same manner as the reference Clostridial domain on which the naturally-occurring Clostridial domain variant is based, and can be substituted for the reference Clostridial domain in any aspect of the present invention.

A naturally-occurring Clostridial domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial domain on which the naturally-occurring Clostridial domain variant is based. A naturally-occurring Clostridial domain variant can also substitute at least 10 contiguous amino acids, at least 15 contiguous amino acids, at least 20 contiguous amino acids, or at least 25 contiguous amino acids from the reference Clostridial domain on which the naturally-occurring Clostridial domain variant is based, that possess at least 50% amino acid identity, 65% amino acid identity, 75% amino acid identity, 85% amino acid identity or 95% amino acid identity to the reference Clostridial domain on which the naturally-occurring Clostridial domain variant is based, so long as the biological or biochemical activity of the naturally-occurring Clostridial domain is substantially preserved. It will also be understood that conservative amino acid insertions and deletions can also be made so long as the characteristic function and identity of the domain is not substantially altered.

Due to the degeneracy of the genetic code, one of ordinary skill in the art will recognize that these amino acid sequences may be encoded by a finite set of different DNA molecules having different, but defined, nucleotide sequences. For example, degenerate nucleotide sequences encoding a given peptide or protein may have different codons adapted or selected to favor expression in a particular host cell. Using this information one can construct an expressible open nucleic acid reading frame for assembly of a nucleic acid molecule comprising any combination of these amino acid domain-encoding regions, either alone or with additional nucleic acid sequences, inserted into a suitable expression vector and subsequent expression within a chosen host cell. For example, International Patent Publication WO01/14570 discloses methods of making single-chain, cleavable recombinant modified or unmodified Clostridial neurotoxin derivatives and chimeric and hybrid forms thereof using such methods. Additional publications disclosing methods of making expressible recombinant neurotoxins and derivatives thereof include U.S. Pat. Nos. 5,989,545; 6,203,794; 6,395,513; U.S. Publication Numbers U.S. 2003/0166238; U.S. 2002/169942; U.S. 2004/176299; U.S. 2004/126397; U.S. 2005/035730; U.S. 2005/068494; U.S. 2006/011966; International Patent Applications WO95/32738; WO 99/55359; WO96/33273; WO98/07864; WO99/17806; WO98/07864; WO02/44199; WO02/40506, and U.S. patent application Ser. No. 13/644,386, filed Oct. 4, 2012. These and all other patents, patent publications, and non-patent publications cited in this patent application, whether or not specifically indicated as such, are hereby individually incorporated by reference as part of this specification.

The use of recombinant DNA techniques permits the construction of modified Clostridial neurotoxins having different or modified functional properties from the naturally-occurring toxin subtypes and strains thereof.

For example, altering the naturally-occurring amino acid sequence of the native neurotoxin light chain and/or adding a different therapeutic moiety permits the construction of transport proteins designed to carry a therapeutic agent within a neuron. See U.S. Pat. No. 6,203,794 (hereby incorporated by reference herein).

Altering the targeting (cell-binding) domain permits the toxin to be transported within pancreatic cells, such as acinar cells, thereby preventing secretion of activated digestive enzymes by such cells, See U.S. Pat. No. 6,843,998 (hereby incorporated by reference herein), or sensory afferent neurons, thereby preventing neurotransmitter, cytokine and pain peptide release and thus providing relief from pain; see U.S. Pat. No. 6,395,513 (hereby incorporated by reference herein.)

In addition, U.S. Pat. No. 7,422,877 (hereby incorporated by reference herein) discloses the creation of chimeric neurotoxin derivatives comprising, for example, the binding domain and the translocation domain (or modified versions thereof) of one neurotoxin subtype for example, BoNT/A, and the light chain region of another neurotoxin subtype, for example, BoNT/E. It will be seen that given the general structural homology between the neurotoxin subtypes, any combination of the three basic Clostridial neurotoxin domains, may be made in a single amino acid chain (or in cleaved di-chain molecules). Therefore, for example, a binding domain from any of neurotoxin subtypes A, B, C1, D, E, F, G, or TeTX may be independently combined with a translocation domain from neurotoxin subtypes A, B, C1, D, E, F, G, or TeTX, and further independently combined with a endopeptidase domain from any of neurotoxin subtypes A, B, C1, D, E, F, G or TeTX. This can be done, for example, by recombinant construction and expression of a single chimeric chain which is subsequently cleaved to yield the dichain toxin, or by separate expression of single H and L chains, which are then combined by, for example, creation of an interchain disulfide bond and subsequently purified. Furthermore, using such techniques, the activity of various domains may be altered (for example, mutations can be introduced in an LC domain to destroy the protease activity of the LC), or the naturally-occurring domains may be replaced with other moieties, as described elsewhere herein, where for example, the HC domain of BoNT/A (or a portion thereof) is mutated or deleted and a targeting ligand (TL) appended.

When discussing the three general neurotoxin domains of each Clostridial neurotoxin subtype (binding, translocation and endopeptidase), it will be understood that Clostridial neurotoxin research is a well-developed field, and the correlation of the amino acid sequences comprising each of these domains with their functions is well known. Reference to each of these terms ("translocation domain", "binding domain", and "protease", "endopeptidase", "LC" or "light chain" domain) shall be understood to include the corresponding domains contained in any of the amino acid sequences of Clostridial neurotoxin subtypes listed in SEQ ID NO: 7-14 as listed in Table 2, as well as conservatively modified and optimized variants of these sequences or domains within these sequences.

Additionally, the subdivision of these general domains into subdomains is also known. For example, the subdivision of binding domain $H_C$ into subdomains $H_{CN}$ (the amino-terminal portion of the domain, corresponding approximately to amino acids 871-1091 of BoNT/A) and $H_{CC}$ (the carboxy-terminal portion of the $H_C$ domain, corresponding approximately to amino acids 1092-1296 of BoNT/A) is also well known. See e.g., Lacy D B and Stevens R C, Sequence Homology and Structural Analysis of the Clostridial Neurotoxins, 1999, J. Mol. Biol. 291:1091-1104. Subdomain $H_{CN}$ is highly conserved among botulinum toxin subtypes, however, little is known about its function. The $H_{CC}$ subdomain is less conserved.

Additionally, the nucleotide and amino acid sequences of each of these domains and subdomains are known and have been disclosed in this specification, and therefore using this disclosure in combination with knowledge of the genetic code, nucleotide sequences encoding a protein to be expressed can be made. It would, of course, be a matter of routine for a person of ordinary skill in the art in view of this specification, to immediately envision other nucleotide sequences encoding the indicated polypeptides. Also, due to the redundancy of the genetic code, a finite number of nucleotide sequences are possible for each polypeptide. Further, it is clear that nucleic acids can be synthesized that comprise conservatively modified variants of these nucleotide sequences (or unique portions of them) in the region of homology containing no more than 10%, 8% or 5% base pair differences from a reference sequence.

Further, it will be understood that the amino acid sequences set forth in Table 2 and elsewhere in this specification or the associated sequence listing provide a full disclosure of any and all nucleotide sequences encoding these amino acid sequences and indicated regions thereof. A nucleotide sequence encoding an endopeptidase domain, translocation domain, or binding domain (including any subdomain) of a given neurotoxin subtype may respectively have 60% or greater, or 65% or greater, or 70% or greater, or 75% or greater, or 80% or greater, or 85% or greater, or 90% or greater, or 95% or greater, or 100% identity to any of such reference amino acid sequence regions listed in Table 2 or elsewhere.

Botulinum neurotoxins are expressed by Clostridial cells which also produce one or more non-toxin "neurotoxin associated proteins" or NAPs that non-covalently associate with the neurotoxin to form hemagglutinin complexes, also known as progenitor complexes. These NAPS help the neurotoxin resist protease degradation in the intestine when it is ingested in contaminated food.

The NAP proteins include three hemagglutinin (HA) proteins (HA1, HA2 and HA3), and a non-toxic, nonhemagglutinin protein (NTNH). BoNT types A2, E and F do not have the HA genes, and only produce a 12S (about 300 kDa) complex comprising BoNT and NTNH. "S" stands for Svedberg unit, a unit of centrifugal sedimentation rate. Types B, C and D produce 12S and 16S (about 500 kDa) complexes; the 16S complex includes BoNT, NTNH, HA1, HA2 and HA3. Type A1 has the 12S and 16S complexes plus a 19S complex of about 900 kDA, which may represent a dimer of 16S complexes.

Currently, BoNT/A1- and/B-hemagglutinin complexes have been approved for such clinical uses. The therapeutic benefits of BoNT/A1 complex are more persistent than that of BoNT/B due to its protease having a longer life-time in neurons.

As indicated above, BoNTs consist of a light chain-associated protease domain (LC) which is linked to a heavy chain (HC) through a single covalent disulphide bond and additional non-covalent bonds. A carboxy terminal (C-terminal) moiety of HC ($H_C$) binds to its specific acceptors expressed on various nerve types, including motor, autonomic and sensory neurons. When bound to a target cell the BoNT molecule is transported into vesicles by endocytosis; the amino terminal (N-terminal) half of HC ($H_N$) forms a channel that allows the LC to translocate from 'endosomal-like' membrane vesicles into the cytosol. Thereafter, the LC cleaves a specific SNARE protein substrate, thereby destroying the SNARE's ability to mediate vesicle-membrane fusion, and thus neurotransmitter, cytokine and pain peptide release from the cell.

The LCs of the various BoNT serotypes are similar, but not identical, and two different LCs may cleave different SNARE proteins, or cleave the same SNARE protein differently. For example, LC/A, LC/C, and LC/E cleave SNAP-25; LC/B, LC/D, LC/F, and LC/G cleave synaptobrevin-2 (VAMP-2); additionally, LC/C cleaves syntaxin, another SNARE protein which has been reported to be required for cell division. The LC of TeTx cleaves VAMP-2. The LCs of each serotype cleave their substrate at unique position in the molecule.

For example, the light chain of BoNT/A (LC/A) removes 9 amino acids from the C-terminus of SNAP-25, whereas the LC/E deletes a further 17 C-terminal residues and, thus, gives a more disruptive blockade of neuro-exocytosis by destabilising stable SNARE complexes (Meng et al., 2009; Wang et al., 2011). For example, the inhibition of neurotransmitter release by LC/A can usually be reversed by elevating $Ca^{2+}$ influx, but not in the case of LC/E, presumably due to the greater destruction of the SNAP-25 substrate. However, despite the greater "robustness" of activity by LC/E, because LC/E induces only short transient neuromuscular paralysis, its clinical applications are limited.

It is highly desirable to create a therapeutic having new properties. For example, therapeutics in which two or more light chain endopeptidases derived from more than one serotype may combined in a BoNT or TeTx derivative in which each light chain is active and recognizes a different amino acid sequence in its substrate SNARE protein may be designed to target conditions like chronic pain, chronic inflammatory conditions (including arthritis), and/or conditions involving cytokine release.

In one example, a therapeutic is designed combining the powerful protease of LC/E combined with the long-lasting action of LC/A. This is particularly important for improving the efficacy of BoNT/A for treating chronic pain, including tension headaches/migraines, and chronic inflammatory diseases such as arthritis because BoNT/A complex on its own has been found to be effective in some, but not all, such patients. See e.g., Naumann M. et al. (2008) ASSESSMENT: BOTULINUM NEUROTOXIN IN THE TREATMENT OF AUTONOMIC DIS- ORDERS AND PAIN (AN EVIDENCE-BASED REVIEW): REPORT OF THE THERAPEUTICS AND TECHNOLOGY ASSESSMENT SUBCOMMITTEE OF THE AMERICAN ACADEMY OF NEUROLOGY, Neurology 70:1707-1714 (hereby incorporated by reference herein). Blocking the exocytosis of pain-associated factors such as pain peptides and glutamate may prove useful in treating chronic pain, neuropathic pain and inflammatory conditions.

BoNT/A is unable to block the exocytotic release of pain-stimulating peptides [e.g. calcitonin gene-related peptide (CGRP) and substance P] from sensory neurons when elicited by activating TRPV1 (transient receptor potential vallinoid 1), a cation channel involved in the signalling of most forms of pain (Meng et al., 2007; Meng et al., 2009).

BoNT/E also fails to inhibit the capsasin-stimulated, TRPV1-mediated release of CGRP and substance P from sensory neurons, due to its cell surface acceptor (glycosylated synaptic vesicle protein 2A (SVP2A) and glycosylated SVP2B) being sparse or absent from the sensory neurons. However, a chimeric protein in which the $H_C$ (receptor-binding domain) of BoNT/E is replaced by its counterpart from BoNT/A is able to block the release of these pain-mediating peptides, indicating that the BoNT/A cell surface receptor facilitates the endocytosis and delivery of LC/E into nociceptive C-fibres.

Once inside the neuron, the LC/E protease, removes 26 SNAP-25 amino acid residues, thus preventing the formation of a stable SNARE complex required for neuro-exocytosis (Meng et al., 2009). Although LC/A also cleaves SNAP-25, it only cleaves 9 amino acid residues, and the blockage of exocytotic activity is less complete and stable.

In order to make it practical to clinically exploit such an advantageous feature of the LC/E protease, it is desirable to greatly extend its duration of action.

BRIEF DESCRIPTION OF THE DRAWINGS

FIG. 1 is a schematic for the creation of a composite neurotoxin by creating a gene construct encoding an active LC/E joined to the N-terminus LC/A moiety of BoNT/A via a linker, to generate composite neurotoxin LC/E-BoNT/A, containing two active proteases.

FIG. 3 is a photo of SDS-PAGE electrophoresis showing treatment of purified LC/E-BoNT/A with biotinylated thrombin to create double-chain toxin and remove the His6 (SEQ ID NO: 15) tag. The symbols+ and – respectively indicate treatment with or without the agent dithiothreitol (DTT) to reduce the disulphide bond linking the LC/E-LC/A and HC/A chains.

FIG. 4 is a photo of Western blots in which serial dilutions of BoNT/A (upper gel) and LC/E-BoNT/A (lower gel) are assayed for their ability to cleave the SNARE protein SNAP-25 in cultured rat cerebellar granule neurons (CGNs).

FIG. 5 shows the duration of muscle paralysis in gastrocnemius muscle injected with LC/E-BoNT/A, BoNT/E or BoNT/A, in which the maximal tolerated dose ($TD_{max}$) is plotted versus length of time in days.

FIG. 8A is a schematic of a dual-protease polypeptide of the present invention. This polypeptide inactivates two different SNARE proteins: VAMP by LC/B and SNAP-25 by LC/A. A synthetic LC/B gene is fused to the 5-terminus of BoNT/A via a linker sequence (encoding "DI" residues) to generate the composite neurotoxin LC/B-BoNT/A. The latter also contains two thrombin recognition sequences.

FIG. 8B SDS-PAGE gel stained by Coomassie blue illustrating the purification of His$_6$-tagged LC/B-BoNT/A by IMAC, using Talon® Superflow Resin (manufactured by Clonetech Laboratories, Inc.).

FIG. 8C SDS-PAGE of IMAC-purified LC/B-BoNT/A following treatment with biotinylated thrombin to create di-chain (DC) toxin. The symbols + and – respectively indicate treatment with or without the reducing agent dithiothreitol (DTT).

FIG. 8D shows a Western blot of an SDS-PAGE gel in which serial dilutions of LC/B-BoNT/A are incubated with rat CGNs at 37° C. for 24 h. The lysates are then assayed using anti-SNAP-25 and anti-VAMP 2 antibodies to monitor the toxin's cleavage of the two SNARE proteins SNAP-25 and VAMP 2. Syntaxin 1, probed by its specific antibody and unrecognized by either LC/B or LC/A, acted as an internal loading control.

FIG. 8E Dose response curves for LC/B-BoNT/A showing cleavage of SNAP-25 (rectangle) and, VAMP 2 (inverted triangle) at higher concentrations of the LC/B-BoNT/A toxin.

FIG. 9 is another example of the present invention in which a multi-SNARE cleaving therapeutic candidate has the ability to inactive all three major types of SNARE proteins: SNAP-25 and syntaxin 1-3 by LC/C1 and VAMP1-3 by LC/D. DI is a linker between LC/D and LC/C1.

DETAILED DESCRIPTION OF THE INVENTION

Figure 2A:
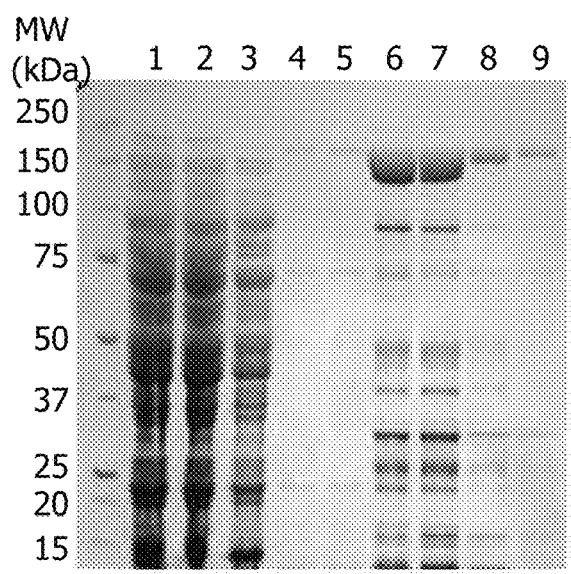
FIG. 2A is a photo of SDS-PAGE electrophoresis showing the purification of the His6-tagged ("His6" disclosed as SEQ ID NO: 15) LC/E-BoNT/A construct by immobilized metal affinity chromatography (IMAC), using Talon® Superflow Resin (manufactured by Clonetech Laboratories, Inc.), a $Co^{2+}$-charged agarose resin having a high degree of selectivity for the His6 tag (SEQ ID NO: 15).

The present invention is directed to methods and compositions related to therapeutic polypeptide molecules derived from botulinum neurotoxins. In particular, the molecules comprise at least two active endopeptidase domains derived from the light chains of different BoNT serotypes. Very preferably the endopeptidase domains recognize and cleave different amino acid sequences in their substrate. Especially preferably, the endopeptidase domains are derived from two or more BoNT serotypes, or a BoNT serotype and a TeTx LC.

The ability to combine a heavy chain from a selected BoNT with at least two different active Clostridial light chain endopeptidase domains provides engineered therapeutic molecules having enhanced and tailored properties. Such therapeutics are first exemplified by the design and creation of a gene construct encoding a composite of two different BoNT serotypes, and prokaryotic expression/purification of the recombinant protein displaying multiple and synergistic biological activities with therapeutic applications.

Blockage of exocytosis by such multi-endopeptidase therapeutics may have additive activities such as blocking the trafficking of pain-sensing receptors to the surface of sensory neurons. Thus, not only do such therapeutics inhibit the exocytosis of soluble synaptic factors, but may also inhibit the trafficking of proteins that are integral to the neural membrane.

In certain therapeutics not illustrated in the Examples section the naturally occurring binding domain may be altered so that the therapeutic is retargeted to a different or additional cell type. For example, in Aoki et al., U.S. Pat. No. 6,776,990 the binding region of BoNT is replaced with human cholecystokinin, or an analog thereof, thereby targeting the toxin (having only a single endopeptidase) to pancreatic acinar cells. Similarly, in U.S. patent application Ser. No. 13/644,386, filed Oct. 4, 2012, a targeting ligand replaces the naturally occurring binding domain in certain examples. In one such example a gene encoding the human interleukin-1 receptor antagonist (IL-1RA) is used to replace the naturally occurring $H_C$ region or part thereof, thereby targeting cytokine-secreting cells.

The presently preferred molecule exemplifying the invention is based on a novel concept for creating nucleic acid constructs that express a protein comprising the LC of BoNT/E fused to the LC/A moiety of active recombinant BoNT/A using molecular biological methods. This unique molecule comprises LC/E-BoNT/A (shown in FIG. 1) which binds to neuronal BoNT/A acceptors (e.g. synaptic vesicle protein 2 and/or gangliosides), undergoes acceptor-mediated endocytosis and translocates to the cytosol, where the SNARE protein SNAP-25 is effectively cleaved, resulting in inhibition of neurotransmitter, cytokine and pain peptide release. By "effectively cleaved" is meant wherein the majority of SNAP-25 molecules have a sufficient number of amino acids cleaved to prevent the reversal of exocytotic blockade by elevating $Ca^{2+}$ influx; for example, such as results from cleavage of SNAP-25 by LC/E.

The above-noted constructs are preferably designed to contain a short sequence encoding specific amino acid residues, situated between HC and LC of /A, that are selectively recognised and cleaved by a thrombin protease, so the single-chain (SC) recombinant protein obtained can be converted to the di-chain (DC) form in vitro by exposure to thrombin.

Very preferably, the present invention is exemplified by LC/E linked to the LC/A moiety of BoNT/A via a two amino acid linker (for example, aspartic acid-isoluecine; DI), yielding a novel composite toxin. In experiments involving the exposure of sensory neurons to this construct, the proteases was shown to be delivered within the cultured neurons, and the attached LC/E was stabilised which, in turn, produced long-lasting neuroparalysis like LC/A.

Importantly, unlike LC/A, this long-acting molecule produced mainly proteolytic products characteristic of LC/E and blocked the release of pain-mediators evoked by capsaicin from rat cultured sensory neurons, due to the inability of /E-cleaved SNAP-25 to mediate neurotransmitter, cytokine and pain peptide release. Moreover, this composite protein proved more effective than LC/A alone in attenuating pain behaviour in a rat model of neuropathic pain (spared nerve injury-induced).

The exemplary chimeric molecule thus offers major advantages as a therapeutic for treatment of chronic pain: (a) a highly-desirable and greatly-extended life-time of the normally transiently-acting /E protease, by virtue of nerve terminal retention/stabilising motifs present in the attached LC/A; (b) predominant cleavage of SNAP-25 by the /E protease destabilises SNARE complexes and (c) inhibition of TRPV1-mediated exocytosis of pain peptides from sensory neurons. These new findings highlight the anti-nociceptive potential of this proprietary engineered protein which exhibits synergistic compounded effects. Its advantages over the first generation of natural BoNTs have been conclusively demonstrated and, thus, should lead to much improved therapeutics.

Because native BoNTs have only one protease domain, the innovative concept of delivering an extra LC—which either cleaves the same substrate at a different position (or another substrate)—not only significantly boosts its inhibitory properties but the additional stabilising influence of the original LC/A results in a surprising synergistic action, namely greatly extended duration of therapeutic benefit compared to BoNT/E.

In other examples, a different multi-endopeptidase therapeutic is exemplified by the construction of a LC/B-BoNT/A nucleic acid construct using the techniques employed for the construction of the LC/E-BoNT/A nucleic acid. Upon expression of the polypeptide encoded by the LC/E-BoNT/A open reading frame, and nicking of the thrombin sites, the resultant protein cleaves both SNAP-25 and VAMP-2. Cleavage of two SNARE proteins involved in the synaptic fusion ternary complex may result in more effective

EXAMPLES

Example 1

A synthetic BoNT/A gene, having its codons optimised for enhanced expression in *E. coli* and three extra nucleotide (AAA) encoding Lys residue, was cloned into Nde I and Sal I sites of a prokaryotic expression vector pET29a(+) to yield pET-29a-BoNT/A.

pET-29a-BoNT/A was then further modified in order to provide the ability for controlled specific nicking and simultaneous removal of the hexahistadine (His6 (SEQ ID NO: 15)) tag encoded by the pET-29a cloning vector. A nucleotide sequence encoding a thrombin cleavage sites was engineered into the nucleic acid region encoding the HC/LC loop of the toxin. This is shown below in both nucleic acid and amino acid form, as SEQ ID NO: 1 and SEQ ID NO: 2, respectively.

Modified BoNT/A loop nucleotide sequence (SEQ ID NO: 1) and
its encoded amino acid sequence (SEQ ID NO: 2)

Thrombin cleavage site
↓

C V R G I I T S K T K S L V P R G S N K A L N D L C

TGTGTCCGCGGTATTATCACCAGCAAAACCAAATCCTTGGTGCCCCGCGGCTCTAACAAGGCGCTCAATGATTTATGC

Additionally, an additional thrombin site was inserted between the regions encoding the HC/A and His6 (SEQ ID NO: 15) regions of the expressed protein. This is shown below in both nucleic acid and amino acid form, as SEQ ID NO: 3 and SEQ ID NO: 4, respectively.

Nucleotide sequence fused to the 3' end of
BoNT/A gene (SEQ ID NO: 3) and
its encoded amino acid sequence (SEQ ID NO: 4)

Thrombin cleavage site
↓

1
K V D K L L V P R G S K L Q L E H H H H H H *

AAAGTCGAC<u><u>AAGCTT</u></u>CTGGTACCGCGCGGCAGCAAACTGCAG<u><u>CTCGAG</u></u>CACCACCACCACCACCACTGA

1

Sal I  HindIII                    Pst I  Xho I

The nucleotide sequence provided above contains the following regions, from left to right, respectively:
a) nucleotides 1-3: AAA codon inserted encoding additional Lys to provide an optional trypsin cleavage site, in order to remove the C-terminal His6 (SEQ ID NO: 15);
b) single underline: Sal I restriction endonuclease site;
c) double underline: Hind III restriction endonuclease site
d) bold: thrombin recognition sequence;
e) single underline: Pst I restriction endonuclease site;
f) double underline: Xho I restriction endonuclease site;
g) nucleotides 49-66: nucleotide region encoding a His6 (SEQ ID NO: 15) tag. The aligned amino acid sequences are displayed above the corresponding nucleotides. The arrow indicates the thrombin cleavage site, and the asterisk denotes the translational "stop" codon.

This nucleic acid construct, comprising the BoNT/A open reading frame described above, and comprising both SEQ ID NO: 1 and SEQ ID NO: 3, was termed pET29a-BoNT/A-2T.

A PCR product (amplicon) was amplified from a synthetic nucleic acid encoding the LC/E protease (residues 1-411), and two restriction sites (Nde I and Eco RV) were incorporated during the amplification at the 5' and 3' ends of the nucleic acid amplicon, respectively. This PCR amplicon was then digested by Nde I and Eco RV and cloned into pET29a (+) vector, also digested with Nde I and Eco RV. The resultant intermediate vector construct was named pET29a-LC/E.

The above-noted intact "single chain" open reading frame BoNT gene region of BoNT/A-2T was amplified by PCR using pET29a-BoNT/A-2T as a template with a pair of primers (a bacteriophage T7 terminal reverse primer and a forward primer containing an EcoRV restriction sequence upstream of the BoNT/A 5' coding sequence). The resulting PCR amplicon was digested by EcoRV and Xho I enzymes, purified, and inserted into Eco RV- and Xho I-cleaved pET29a-LC/E plasmid. This final construct was called pET29a-LC/E-BoNT/A, and the open nucleic acid reading frame is disclosed as SEQ ID NO: 5, while the corresponding amino acid sequence is disclosed herein as SEQ ID NO: 6.

Example 2

For expression of LC/E-BoNT/A, the sequence-verified construct was transformed into E. coli strain BL21(DE3), and expressing of the target protein was induced using Studier's auto-induction medium (Studier, F. W., 41 Protein Expr. Purif. 207 (2005)). Partial purification (~60%) of the His6 (SEQ ID NO: 15) tagged protein in the bacteria lysate was achieved with immobilised metal ($Co^{2+}$) affinity chromatograph (IMAC), using Talon superflow resin. A major protein of Mr~200 kDa is eluted by greater than or equal to 50 mM imidazole; this is demonstrated in FIG. 2A, which shows SDS-PAGE and Coomassie blue staining of the gel. Gel lanes are as follows: Lane 1: cleared lysate before application to IMAC column; Lane 2: the IMAC column flowthrough fraction; Lane 3: the IMAC column wash fraction; Lanes 4-9, fractions eluted using imidazole from the IMAC column.

Figure 2B:
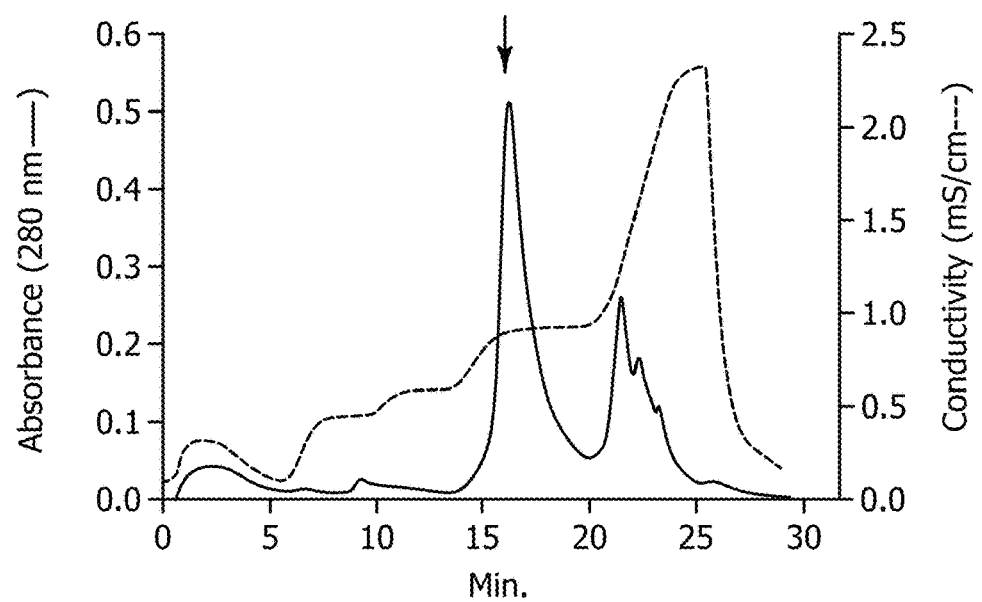
FIG. 2B shows the absorbance and conductivity versus time in an elution profile of pooled LC/E-BoNT/A-containing IMAC fractions subsequently subjected to cation-exchange chromatography.

The pooled IMAC eluted fractions were buffer-exchanged into 0.02 M sodium phosphate buffer (pH 6.5), and then further purified by loading onto a UNO-S1 cation exchange column, followed by washing with up to 150 mM NaCl, and then elution with a NaCl gradient; the toxin was eluted NaCl concentrations of equal to or greater than 220 mM. FIG. 2B shows the elution profile (absorbance at 280 nm) of the LC/E-BoNT/A single chain polypeptide as a function of time, with the increase in conductivity of the NaCl gradient superimposed. The arrow shows the location of the LC/E-BoNT/A-containing absorbance peak.

Example 3

After buffer-exchanging the eluted intact toxin into 25 mM HEPES/145 mM NaCl (pH 7.4), the purified single chain ("SC") protein was stored at −80° C., and aliquots were taken for SDS-PAGE analysis. FIG. 3 shows the results of reducing (+) and non-reducing (−) SDS-PAGE and Western blotting analysis of the purified polypeptide, confirming that this purified protein was indeed expressed in a SC form, as revealed by a single band migrating with an apparent molecular weight of about 200 kDa. This band was seen in either the absence or presence of reducing agent. See e.g., lanes SC (−) and SC (+) of the Coomassie Brilliant Blue-stained gel photo of FIG. 3.

Nicking of this SC polypeptide was attempted by incubation with biotinylated thrombin (1 unit/mg of protein) at 22° C. for 3 hours; the thrombin protease is then removed by treating the sample with streptavidin agarose. A band having an apparent molecular weight of about 100 KDa appears after thrombin treatment of the protein in samples run on an SDS-PAGE gel under reducing conditions; the ~200 KDa band is not seen under these conditions, but is present in gels run under non-reducing conditions, while the ~100 KDa band is absent in these latter samples. See e.g., lanes DC (−) and DC (+) of the Coomassie Brilliant Blue-stained gel photo of FIG. 3.

The ~100 KDa band is believed to represent both the LC/E-LC/A and the HC/A chains, which have similar sizes. The identities of the polypetides in this band are confirmed by Western blotting of SDS-PAGE gels run on nicked and unnicked LC/E-BoNT/A using antibodies specific against each of the postulated single chain polypeptides LC/E and BoNT/A.

As shown in FIG. 3, the nicked sample continues to migrate at ~200 kDa in the absence of reducing agent, indicating that the inter-chain disulphide bond between LC/E-LC/A and HC/A was formed, and persists, in all of the samples as shown in the lanes of the Western blots marked (−) and developed using either anti-LC/E or anti-BoNT/A antibodies. Thus, SDS-PAGE and Western blotting under reducing and non-reducing conditions highlight the specific nicking at the loop region that occurs without degradation of the composite toxin. A slight difference in the mobility of the un-nicked and nicked protein is due to removal of the His6 (SEQ ID NO: 15) tag in the thrombin-treated samples; this was confirmed using a specific antibody against this tag. See the Western blot using the anti-His6 (SEQ ID NO: 15) antibody of FIG. 3, in which the His6 (SEQ ID NO: 15) tag is undetectable. This experiment therefore also demonstrated that thrombin protease can simultaneously nick the toxin between the linked cysteine residues of the disulphide bond between the HC and the first LC, and remove the His6 (SEQ ID NO: 15).

Example 4

Recombinantly-produced LC/E-BoNT/A and BoNT/A were each incubated overnight at 10-fold serially diluted concentrations from 0.01 pM to 1000 pM of toxin with cultured rat cerebellar granule neurons (CGNs). These cells are dissociated from the cerebella of 7-8-day-old rats and suspended at about $1 \times 10^6$/ml in 3 parts of basal Eagle's medium and 1 part of 40 mM HEPES-NaOH, pH 7.3, 78.4 mM KCl, 37.6 mM D-glucose, 2.8 mM $CaCl_2$, 1.6 mM $MgSO_4$, and 1.0 mM $NaH_2PO_4$, as well as 1× N2 supplement, 1 mM L-glutamine, 60 units/ml penicillin, 60 μg/ml streptomycin, and 2% (v/v) horse dialyzed serum. An aliquot (1 ml) of this cell suspension is added to each of 16-mm-diameter poly-D-lysine coated well (i.e. 24-format) and cytosine-β-D-arabinofuranoside (40 μM) added after culturing for 20-24 h in 5% (v/v), $CO_2$; the neurons are maintained by replacement every 10 days with the same freshly prepared medium. Where specified, the neurons are exposed to either BoNT/A or LC/E-BoNT/A (0.2-μm filter sterilized) in culture medium for 24 h.

After 24 hours' incubation with BoNT/A or LC/E-BoNT/A protein, cells are then harvested and subjected to SDS-PAGE and Western blotting using an anti-SNAP-25 antibody recognising intact SNAP-25, as well as both LC/A-cleaved SNAP-25 and LC/E-cleaved SNAP-25. The SNARE protein syntaxin 1 was used as a positive internal loading control.

Western blotting was performed using anti-SNAP-25 antibody. As can be seen in FIG. 4, LC/E-BoNT/A was nearly as active as BoNT/A in cleaving intact SNAP-25, with significant cleavage occurring at concentrations of toxin above 1 μM in each case. Notably, as can be seen, treatment of CGNs with LC/E-BoNT/A also gives a LC/A cleavage product when below about 1 μM of toxin is used. This cleavage product ("SNAP-$25_A$") appears to be substantially further cleaved to the cleavage product of LC/E ("SNAP-$25_E$") by the co-delivered LC/E protease when the LC/E-BoNT/A toxin's concentrations are raised above about 0.01 nM (FIG. 4). These results suggest that the BoNT/A heavy chain translocation domain is capable of delivering both covalently-linked LC/A and LC/E proteases to the cytosol of CGNs, where the proteases remain active to cleave SNAP-25, thereby wholly or partially inactivating the SNARE protein.

Example 5

The specific neurotoxicity of LC/E-BoNT/A is determined by intraperitoneal injection into mice in the manner described in Maisey, E. A., et al., 177 EUR. J. BIOCHEM. 683-691(1988), hereby incorporated by reference. The lowest amount of toxin that kills 50% of mice within 4 days is defined as one minimal lethal dose (mLD50). The specific activity of the toxins can be expressed as the number of mLD50 units/mg of toxin.

The mLD50 of the LC/E-BoNT/A preparation is observed to be $0.7 \times 10^8$. This specific activity is between that observed for recombinant BoNT/E ($0.4 \times 10^8$) and that observed for recombinant BoNT/A ($2 \times 10^8$). The duration of neuroparalytic action in vivo was assessed using a mouse digit abduction score (DAS) assay, described in e.g., Aoki, K. R., 39 TOXICON 1815-1820 (2001), hereby incorporated by reference.

Recombinant LC/E-BoNT/A is injected into mouse gastrocnemius muscle at a dose of 0.5 $mLD_{50}$ unit, which is the maximum tolerated dose that may be administered to the experimental animals without producing systemic symptoms. This dosage of LC/E-BONT/A caused paralysis for about 27 days; similar to the effect induced by 6 units of native BoNT/A; see FIG. 5. The long-lasting action of the LC/E-BONT/A protein compared to BoNT/E is apparently is due to the ability of the LC/A moiety in the fusion protein to stabilise the attached LC/E moiety; BoNT/E alone gives much shorter paralysis than other toxins; see the comparison of BoNT/E versus LC/E-BoNT/A in FIG. 5.

Example 6

The anti-nociceptive potential of the LC/E-BONT/A protein is examined using trigeminal ganglionic neurons (TGNs). These cells are a good model for this experiment due to their involvement in pain propagation and the fact that these cells in culture provide a good model for investigating the release of pain peptides (CGRP, SP) triggered by different stimuli; see e.g., Bacccaglini and Hogan, 80 PROC NATL ACAD SCI U.S.A. 594-598 (1983). Capsaicin, isolated from chili peppers, activates TRPV1, which is mainly expressed on the C-fibre of sensory neurons. Thus, the ability of the composite toxin to block the release of CGRP evoked by its agonist, capsaicin, should be a good indication of its inhibitory activity.

BoNT/A only removes 9 amino acid residues from the C terminus of the SNARE protein SNAP-25 (the "/A-truncated" SNAP-25 cleavage product), and does not affect the CGRP exocytosis elicited by capsaicin in TGNs. By contrast, the removal of 17 additional residues by the LC/E protease (resulting in the "/E-truncated" SNAP-25 cleavage product), blocks this capsaicin-stimulated release of CGRP; see e.g., Meng et al., 29 J NEUROSCI 4981-4992 (2009), hereby incorporated by reference.

Since the main SNAP-25 cleavage product of the long-acting toxin, LC/E-BoNT/A, is the "/E-truncated" SNAP-25 cleavage product, rather than the "/A-truncated" SNAP-25 cleavage product in CGNs (see FIG. 4), it is expected that LC/E-BoNT/A will block the release of the CGRP pain peptide.

Briefly, TGNs are dissected from postnatal day 5 Wistar rats after being deeply-anesthetized with intraperitoneal injection of Dolethal (50 mg/kg body weight). The tissue is placed in ice-cold L15 medium, and then washed twice in ice-cold sterile CMF-HBSS before centrifugation at 170 g for 1 minute. After chopping the tissue into small pieces and passing through 10-ml Falcon pipettes pre-coated with L15 medium, the tissue is incubated with shaking at 37° C. for 30 minutes in a 1:1 mixture of calcium- and magnesium-free Hanks Balanced Salt Solution (CMF-HBSS) containing 2.4 U/ml dispase II and 1 mg/ml collagenase I. The suspension is then gently triturated through 10-ml Falcon pipettes pre-coated with L15 medium until cloudy, before adding 1 mg/ml DNase I for 15 minutes.

Following centrifugation at 170 g for 5 minutes, the cell pellet is suspended and washed three times in culture medium [Ham's F12 solution (Sigma-Aldrich, St. Louis, Mo.) containing 10% (v/v) heat-inactivated fetal bovine serum (FBS), 100 IU/ml penicillin and 100 µg/ml streptomycin]. Cells are seeded onto 24-well plates precoated with poly-L-lysine (0.1 mg/ml) and laminin (20 µg/ml) in F12 medium supplemented with nerve growth factor (NGF) (50 ng/ml) and maintained in a $CO_2$ incubator at 37° C. After 24 hours (and every day thereafter) the culture supernatant is replaced with fresh culture medium containing the antimitotic agent cytosine-β-D-arabinofuranoside (10 µM).

After overnight incubation of rat TGNs at 37° C. with serial dilutions of LC/E-BoNT/A, the extent of cleavage is monitored by SDS-PAGE followed by Western blotting using an anti-SNAP-25 antibody capable of binding to intact as well as A-truncated and E-truncated products.

Figure 6A:
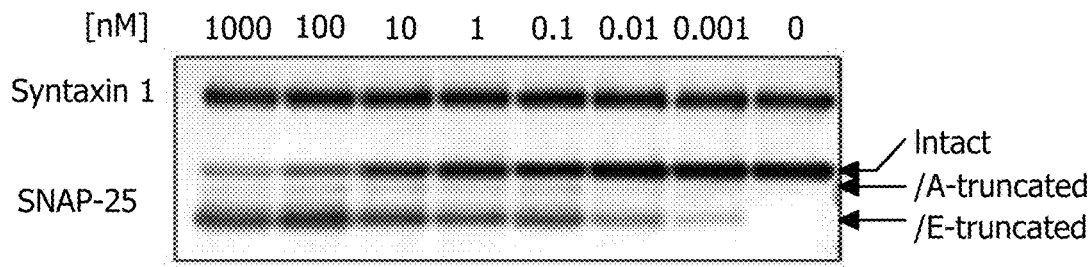
FIG. 6A is a photo of a Western blot in which serial dilutions of LC/E-BoNT/A are incubated with rat TGNs (trigeminal ganglion neurons) overnight, then the lysates assayed using anti-SNAP-25 and anti-syntaxin antibodies for the ability of LC/E-BoNT/A to cleave SNAP-25 (mainly to yield the 26 residue truncated SNAP-25 cleavage product produced by LC/E), but not syntaxin.

As shown in FIG. 6A, LC/E-BoNT/A gives a dose-dependent cleavage of SNAP-25 with mainly "/E-truncated" SNAP-25 cleavage products.

Figure 6B:
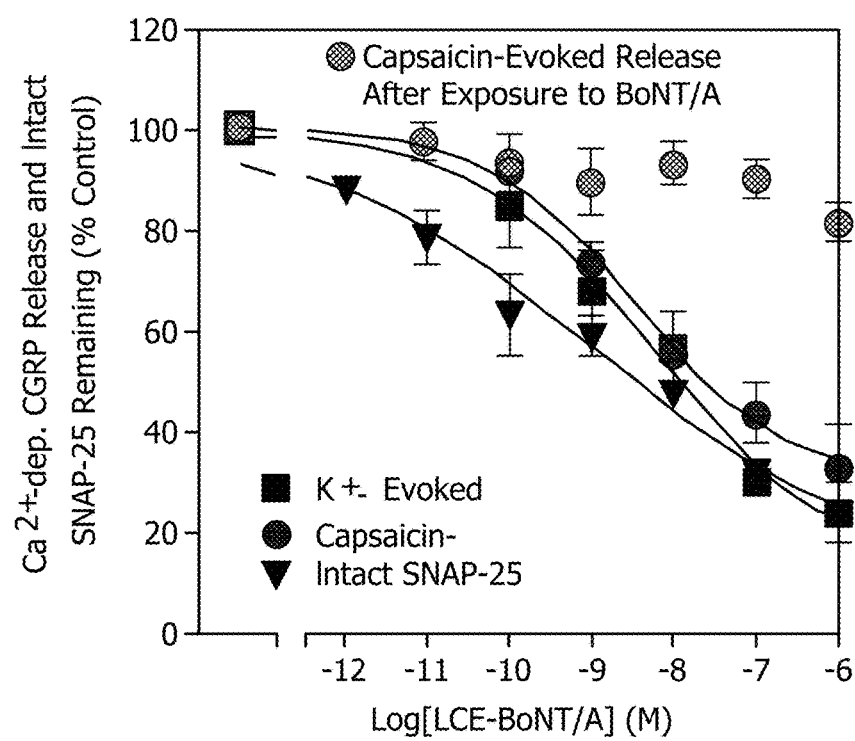
FIG. 6B is a dose response curve by LC/E-BoNT/A showing a) the cleavage of SNAP-25 and b) the inhibition of CGRP release evoked by 60 mM KCl or c) capsaicin in rat TGNs, and the failure of BoNT/A to significantly reduce CGRP release evoked by capsaicin in TGNs incubated with BoNT/A.

Additionally, as expected, the composite toxin blocks the release of CGRP by TGNs evoked by 60 mM KCl or capsaicin in a dose-dependent manner (FIG. 6B). $Ca^{2+}$-dependent CGRP release is stimulated by treatment with 60 mM KCl in HBS (isotonically balanced with NaCl). For stimulation with capsaicin, stocks (1 mM) were prepared in ethanol or dimethyl sulfoxide, respectively, and diluted in BR-HBS to the required concentrations. In all cases, the final concentration of vehicle is kept at 0.1%; this is also included in BR-HBS when measuring basal efflux.

Cells were stimulated with $K^+$ or capsaicin and release of CGRP monitored for 30 min. To determine the amounts of CGRP released, 0.1 ml of sample were added to 96-well plates coated with a monoclonal antibody against CGRP, and enzyme immunoassay was performed following instructions for the kit.

The results show the ability of the LC/E-BoNT/A polypeptide to inhibit the release of pain peptides from large dense-core vesicles, while similar treatment of cells with BoNT/A failed to inhibit the release of CGRP upon the activation of the TRPV1 cation channel. See FIG. 6B.

Example 7

The anti-nociceptive activity of LC/E-BoNT/A was evaluated in a rat model of persistent peripheral neuropathic pain, namely the spared nerve injury (SNI) assay. This model is based upon the observation that virtually all neuropathic pain (except the special case of phantom limb pain, caused by complete lesion by amputation) results from a partial nerve injury. These neuropathic pains include diabetic neuropathy, postherpeutic neuralgia, toxic neuropathies, compression neuropathies and trauma, and are characterized by spontaneous lancinating, burning pain and shock-like pain as well as pain hypersensitivity including tactile allodynia, pin prick hyperalgesia and hyperpathia.

SNI surgery is conducted on anesthetized adult rats (such as Spague-Dawley rats), and involves the ligation and transection of two of the three terminal distal branches of the sciatic nerve (the tibial and common peroneal nerves), which leaving the third branch (the sural nerve) intact; see Decosterd, I. & Woolf, C. J., 87 PAIN 580-587 (2000) incorporated by reference herein. This model has the advantage of being both technically easy to perform, and subject to minimal variability in the degree of damage produced.

The toxins are injected into the plantar (palm) side of the distal hindlimb. The maximum intra-plantar dosages of LC/E-BoNT/A and BoNT/A (without affecting the locomotor function) are found to be 75 and 15 mouse LD50 units/kg, respectively. Rats with SNI show a long-lasting neuropathic pain-like behaviour in contrast to sham control rats (which are subjected to exposure of the sciatic nerve without any lesion).

Figure 7A:
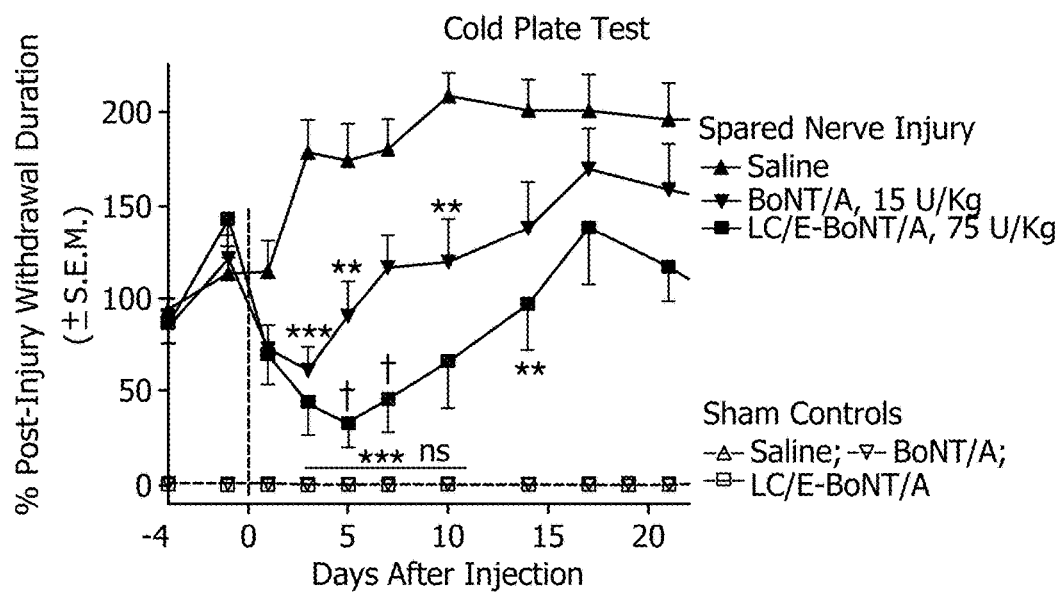
FIG. 7A is a plot of duration of anti-nociceptive activity in a rat model, the spared nerve injury (SNI) test, on animals treated with saline, BoNT/A or LC/E-BoNT/A, followed by placing the paw in a cold (4° C.) plate and measuring the time required for the rat to withdraw its paw from the plate, carried out from 4 days pre-surgery to about 21 days post surgery.

The two models of neuropathic pain are tests of cold allodynia and mechanical allodynia. In the first test, that of cold hypersensitivity, the operated paw is contacted with a cold plate at 4° C., and the paw withdrawal duration is recorded at various time points, as shown in FIG. 7A. As a measure of cold hypersensitivity modulation, post-treatment values are expressed as a percentage of pre-treatment values.

As FIG. 7A shows, the cold hypersensitivity is efficiently reduced by LC/E-BoNT/A for 2 weeks after treatment ($P<0.001$ compared to saline-treated), particularly for the first 10 days. The anti-nociceptive effect of LC/E-BoNT/A is significantly greater than that induced by BoNT/A ($P<0.05$ at 5 and 7 days after injection). No cold-induced allodynia is seen in sham controls, whether given toxin or saline.

In the second test, mechanical allodynia is measured by placing the animal on an elevated wire grid, and stimulating the plantar surface of the treated paw with a set of von Frey hairs to determine how much sensory stimulation can be tolerated before pain (indicated by a brisk withdrawal of the paw) is detected. Von Frey hairs (or monofilaments) are calibrated to provide an approximately logarithmic scale of actual force, and a linear scale of perceived intensity. The mechanical threshold is expressed as 50% of the average minimum grams of force required to cause paw withdrawal.

Figure 7B:
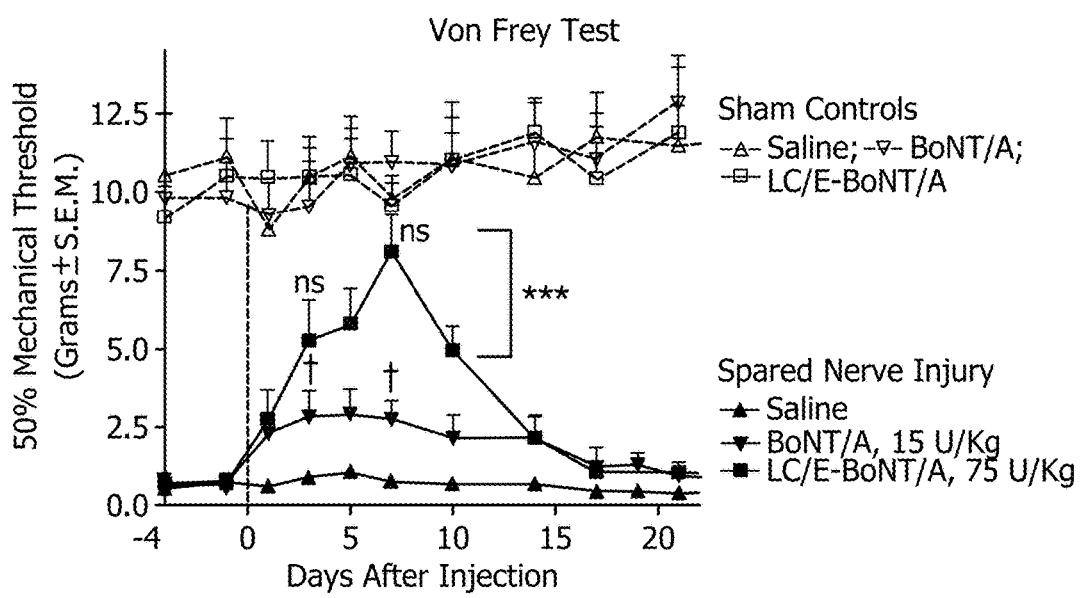
FIG. 7B is a plot of duration of anti-nociceptive activity in a rat model, the spared nerve injury (SNI) test, on animals treated with saline, BoNT/A or LC/E-BoNT/A, followed by measuring the induced allodynia by sensitivity to application of calibrated von Frey hairs onto the plantar surface of the hind paw, carried out from 4 days pre-surgery to about 21 days post surgery.

As shown in FIG. 7B, mechanical thresholds is dramatically decreased by nerve injury (compare the sham controls with the SNI rats given only saline). Encouragingly, LC/E-BoNT/A begins to reverse this mechanical hypersensitivity within 2 days after injection, and a maximum of analgesic effect is seen at 7 days post-treatment. Significantly higher mechanical thresholds than the saline-treated rats are recorded from 3 to 10 days after injection (P<0.001 vs saline). Moreover, even though treatment with BoNT/A induces a modest increase of post-injury mechanical thresholds, LC/E-BoNT/A is found to be significantly more effective (P<0.05).

Neither toxin nor saline affected pain behaviour triggered by cold and mechanical stimuli when administered into sham animals (FIG. 7A, B). LC/E-BoNT/A proved much more effective than BoNT/A in reducing cold withdrawal duration (FIG. 7A) and especially, increasing mechanical withdrawal threshold (FIG. 7B). Importantly, injection of LC/E-BoNT/A into rats with SNI normalised sensitivity to cold and mechanical stimuli at days 3 and 7 to values similar to those of all the sham controls. In summary, LC/E-BoNT/A induces potent anti-nociceptive effects in rat models of chronic neuropathic pain.

Example 8

The composite synthetic neurotoxin open reading frame LC/E-BoNT/A gene sequence and its encoded amino acids (SEQ ID NO: 5 and 6, respectively) provided below contains the following regions, respectively (identified with respect to the nucleotide residues): residues 1-1233, LC/E; residues 1240-5130, BoNT/A. The DNA sequence comprising nucleotides (1234-1239) is introduced as a linker and ensures the proper reading frame. The aligned amino acid sequences are displayed above the corresponding nucleotides. A thrombin protease recognition sequence is inserted into the loop between LC/A and HN/A; similarly, another thrombin site was engineered to have a cleavage sequence to the carboxy site of the BoNT/A gene; these allow simultaneous nicking and removal of the C-terminal His6 (SEQ ID NO: 15).

Composite neurotoxin gene (LC/E-BoNT/A) sequence and its encoded amino acids (SEQ ID NO: 5 AND 6)

```
        M   P   K   I   N   S   F   N   Y   N   D   P   V   N   D   R   T   I   L   Y   I   K   P   G   G   C   Q
    1   ATGCCTAAAATCAATTCGTTCAACTATAATGACCCGGTTAACGATCGCACGATCCTGTATATCAAGCCAGGTGGATGTCA      80

E   F   Y   K   S   F   N   I   M   K   N   I   W   I   I   P   E   R   N   V   I   G   T   T   P   Q   D
   81   AGAATTTTATAAATCATTCAACATCATGAAAAATATTTGGATTATCCCGGAACGCAACGTGATCGGCACGACGCCTCAAG    160

F   H   P   P   T   S   L   K   N   G   D   S   S   Y   Y   D   P   N   Y   L   Q   S   D   E   E   K
  161   ATTTTCACCCGCCGACCTCCCTGAAAAATGGCGACAGTTCCTACTATGACCCGAATTATTTACAATCGGATGAAGAAAAA    240

D   R   F   L   K   I   V   T   K   I   F   N   R   I   N   N   N   L   S   G   G   I   L   L   E   E   L
  241   GATCGTTTCCTCAAGATCGTCACGAAAATTTTCAACCGCATCAATAACAATCTGTCCGGTGGCATCTTACTTGAGGAATT    320

S   K   A   N   P   Y   L   G   N   D   N   T   P   D   N   Q   F   H   I   G   D   A   S   A   V   E   I
  321   ATCTAAAGCTAATCCGTATCTGGGGAACGATAATACCCCGGATAATCAGTTCCACATTGGCGATGCGAGCGCTGTGGAAA    400

K   F   S   N   G   S   Q   D   I   L   L   P   N   V   I   I   M   G   A   E   P   D   L   F   E   T
  401   TTAAATTCAGCAACGGCAGTCAAGATATTCTTCTCCCAAACGTGATTATCATGGGGGCTGAACCTGATCTTTTCGAAACT    480

N   S   S   N   I   S   L   R   N   N   Y   M   P   S   N   H   G   F   G   S   I   A   I   V   T   F   S
  481   AATAGTTCCAATATTTCACTGCGCAATAATTATATGCCGTCGAACCATGGCTTTGGCTCAATCGCAATTGTGACGTTCTC    560

P   E   Y   S   F   R   F   N   D   N   S   M   N   E   F   I   Q   D   P   A   L   T   L   M   H   E   L
  561   ACCTGAATATAGTTTTCGTTTTAACGACAACAGCATGAATGAATTTATCCAAGACCCGGCGCTGACTTTGATGCATGAAC    640

I   H   S   L   H   G   L   Y   G   A   K   G   I   T   T   K   Y   T   I   T   Q   K   Q   N   P   L
  641   TGATCCATAGCTTGCACGGCCTGTATGGCGCTAAAGGCATCACTACCAAATACACGATTACGCAAAAACAAAATCCCTTA    720

I   T   N   I   R   G   T   N   I   E   E   F   L   T   F   G   G   T   D   L   N   I   I   T   S   A   Q
  721   ATCACCAACATCCGCGGCACCAACATTGAAGAATTTCTGACCTTCGGCGGAACGGATCTGAACATCATTACATCTGCCCA    800

S   N   D   I   Y   T   N   L   L   A   D   Y   K   K   I   A   S   K   L   S   K   V   Q   V   S   N   P
  801   AAGCAACGACATCTATACCAATCTGTTAGCAGATTATAAGAAAATCGCCAGCAAATTATCTAAAGTTCAGGTCAGCAATC    880

L   L   N   P   Y   K   D   V   F   E   A   K   Y   G   L   D   K   D   A   S   G   I   Y   S   V   N
  881   CGCTGTTAAACCCGTATAAAGATGTGTTCGAAGCGAAATACGGCTTGGACAAAGACGCTAGTGGCATCTATTCCGTCAAT    960

I   N   K   F   N   D   I   F   K   K   L   Y   S   F   T   E   F   D   L   A   T   K   F   Q   V   K   C
  961   ATTAATAAATTTAACGATATTTTCAAAAAATTATATTCCTTCACCGAATTTGATTTGGCCACCAAATTCCAGGTCAAATG   1040

R   Q   T   Y   I   G   Q   Y   K   Y   F   K   L   S   N   L   L   N   D   S   I   Y   N   I   S   E   G
 1041   TCGTCAAACCTATATTGGCCAATACAAATATTTTAAACTGAGCAACCTGCTTAATGATTCCATCTACAATATTAGTGAAG   1120

Y   N   I   N   N   L   K   V   N   F   R   G   Q   N   A   N   L   N   P   R   I   I   T   P   I   T
 1121   GTTACAATATTAATAACCTGAAAGTTAACTTTCGTGGGCAAATGCGAATCTGAACCCCCGCATCATTACACCCATCACG   1200
```

```
              G   R   G   L   V   K   K   I   I   R   F   D   I   M   P   F   V   N   K   Q   F   N   Y   K   D   P   V
1201 GGCCGTGGGTTGGTCAAAAAAATTATTCGCTTTGATATCATGCCGTTCGTAAACAAACAGTTCAACTATAAAGACCCAGT 1280

N   G   V   D   I   A   Y   I   K   I   P   N   A   G   Q   M   Q   P   V   K   A   F   K   I   H   N   K
1281 CAACGGCGTGGACATTGCCTATATCAAAATCCCGAATGCGGGTCAAATGCAGCCCGTGAAAGCATTTAAAAATCCATAACA 1360

I   W   V   I   P   E   R   D   T   F   T   N   P   E   E   G   D   L   N   P   P   P   E   A   K   Q
1361 AAATTTGGGTGATCCCGGAGCGCGATACGTTCACGAACCCGGAAGAAGGAGATTTAAACCCACCGCCTGAGGCTAAACAG 1440

V   P   V   S   Y   Y   D   S   T   Y   L   S   T   D   N   E   K   D   N   Y   L   K   G   V   T   K   L
1441 GTCCCGGTGTCTTACTATGATAGCACATACCTGAGTACCGACAATGAAAAGGACAACTACCTGAAAGGTGTTACCAAACT 1520

F   E   R   I   Y   S   T   D   L   G   R   M   L   L   T   S   I   V   R   G   I   P   F   W   G   G   S
1521 GTTCGAGCGCATTTATTCGACAGATCTCGGTCGCATGTTGCTGACTTCTATTGTGCGCGGCATTCCGTTTTGGGGTGGTA 1600

T   I   D   T   E   L   K   V   I   D   T   N   C   I   N   V   I   Q   P   D   G   S   Y   R   S   E
1601 GCACCATCGATACAGAACTCAAAGTGATTGACACCAACTGCATCAATGTGATTCAGCCTGATGGGAGCTACCGGTCCGAA 1680

E   L   N   L   V   I   I   G   P   S   A   D   I   I   Q   F   E   C   K   S   F   G   H   E   V   L   N
1681 GAGCTTAACCTCGTAATCATTGGCCCGAGCGCGGATATTATCCAATTCGAATGTAAATCTTTTGGGCATGAAGTCCTGAA 1760

L   T   R   N   G   Y   G   S   T   Q   Y   I   R   F   S   P   D   F   T   F   G   F   E   E   S   L   E
1761 TCTGACGCGGAATGGCTATGGATCGACGCAGTATATTCGTTTTTCTCCAGATTTCACATTTGGATTTGAAGAAAGCCTCG 1840

V   D   T   N   P   L   L   G   A   G   K   F   A   T   D   P   A   V   T   L   A   H   E   L   I   H
1841 AAGTTGATACGAACCCTCTTTTAGGCGCGGGAAAATTCGCGACGGACCCAGCGGTGACCTTGGCACATGAACTTATTCAT 1920

A   G   H   R   L   Y   G   I   A   I   N   P   N   R   V   F   K   V   N   T   N   A   Y   Y   E   M   S
1921 GCCGGGCATCGCTTGTATGGAATCGCCATTAACCCGAACCGTGTTTTCAAGGTGAATACGAACGCGTATTACGAGATGTC 2000

G   L   E   V   S   F   E   E   L   R   T   F   G   G   H   D   A   K   F   I   D   S   L   Q   E   N   E
20014 GGGCTTAGAAGTGTCCTTTGAAGAACTGCGCACGTTTGGCGGTCATGATGCAAAATTTATTGATAGTCTGCAAGAAAACG 2080

F   R   L   Y   Y   Y   N   K   F   K   D   I   A   S   T   L   N   K   A   K   S   I   V   G   T   T
2081 AATTTCGGCTGTACTATTACAATAAATTCAAAGACATTGCATCAACCTTAAACAAGGCGAAAAGCATTGTGGGTACCACG 2160

A   S   L   Q   Y   M   K   N   V   F   K   E   K   Y   L   L   S   E   D   T   S   G   K   F   S   V   D
2161 GCTAGCTTACAATATATGAAAAACGTTTTCAAAGAAAAATACCTCCTTAGCGAAGACACTTCCGGCAAATTCTCTGTCGA 2240

K   L   K   F   D   K   L   Y   K   M   L   T   E   I   Y   T   E   D   N   F   V   K   F   F   K   V   L
2241 TAAACTGAAATTTGATAAACTGTATAAAATGCTCACCGAGATCTACACAGAGGATAACTTTGTCAAATTCTTCAAGGTCT 2320

N   R   K   T   Y   L   N   F   D   K   A   V   F   K   I   N   I   V   P   K   V   N   Y   T   I   Y
2321 TGAATCGGAAAACCTATCTGAACTTCGATAAAGCCGTCTTTAAGATCAACATCGTACCGAAAGTTAACTACACCATCTAT 2400

D   G   F   N   L   R   N   T   N   L   A   A   N   F   N   G   Q   N   T   E   I   N   N   M   N   F   T
2401 GATGGCTTTAATCTGCGCAATACGAATCTGGCGGCGAACTTTAACGGCCAGAACACCGAAATCAACAACATGAACTTTAC 2480

K   L   K   N   F   T   G   L   F   E   F   Y   K   L   L   C   V   R   G   I   I   T   S   K   T   K   S
2481 TAAACTGAAAAATTTTACCGGCTTGTTTGAATTTTATAAGCTCCTGTGTGTCCGCGGTATTATCACCAGCAAAACCAAAT 2560

Thrombin cleavage site
                      ↓
              L   V   P   R   G   S   N   K   A   L   N   D   L   C   I   K   V   N   N   W   D   L   F   F   S   P
2561 CCTTGGTGCCCCGCGGCTCTAACAAGGCGCTCAATGATTTATGCATCAAGGTGAACAACTGGGACTTGTTTTTCTCTCCA 2640

S   E   D   N   F   T   N   D   L   N   K   G   E   E   I   T   S   D   T   N   I   E   A   A   E   E   N
2641 TCTGAAGATAATTTTACTAACGACTTGAACAAAGGAGAGGAAATTACTTCCGATACCAACATCGAAGCAGCGGAAGAGAA 2720

I   S   L   D   L   I   Q   Q   Y   Y   L   T   F   N   F   D   N   E   P   E   N   I   S   I   E   N   L
2721 TATTAGCCTGGATCTTATTCAACAATATTACCTGACCTTTAATTTTGATAACGAGCCTGAGAACATTTCCATTGAGAATC 2800

S   S   D   I   I   G   Q   L   E   L   M   P   N   I   E   R   F   P   N   G   K   K   Y   E   L   D
2801 TCAGCTCTGACATCATCGGCCAGCTGGAACTGATGCCGAATATCGAACGCTTTCCTAATGGAAAGAAATATGAATTGGAC 2880

K   Y   T   M   F   H   Y   L   R   A   Q   E   F   E   H   G   K   S   R   I   A   L   T   N   S   V   N
2881 AAATACACCATGTTCCACTATCTCCGCGCGCAGGAGTTTGAGCACGGCAAGTCTCGTATTGCTCTGACCAATTCGGTAAA 2960

E   A   L   L   N   P   S   R   V   Y   T   F   F   S   S   D   Y   V   K   K   V   N   K   A   T   E   A
2961 CGAAGCCCTTTTAAATCCTTCGCGTGTGTACACCTTTTTCTCAAGCGATTATGTTAAAAAAGTGAACAAGGCGACCGAAG 3040

A   M   F   L   G   W   V   E   Q   L   V   Y   D   F   T   D   E   T   S   E   V   S   T   T   D   K
3041 CGGCGATGTTTTTGGGATGGGTGGAACAACTGGTATATGACTTTACGGATGAAACTTCTGAAGTCTCGACCACCGACAAA 3120

I   A   D   I   T   I   I   I   P   Y   I   G   P   A   L   N   I   G   N   M   L   Y   K   D   D   F   V
3121 ATTGCCGATATTACCATTATCATTCCCTATATTGGCCCTGCACTGAACATTGGTAACATGCTGTATAAAGATGATTTTGT 3200
```

```
        G  A  L  I  F  S  G  A  V  I  L  L  E  F  I  P  E  I  A  I  P  V  L  G  T  F  A
3201 GGGCGCCCTGATCTTTTCAGGCGCTGTTATCCTGCTGGAATTTATCCCGGAAATCGCCATTCCAGTACTCGGTACCTTTG 3280

L  V  S  Y  I  A  N  K  V  L  T  V  Q  T  I  D  N  A  L  S  K  R  N  E  K  W
3281 CGCTGGTGTCCTATATCGCAAACAAAGTTTTGACTGTCCAGACGATCGACAACGCGCTCAGTAAACGTAACGAAAAATGG 3360

D  E  V  Y  K  Y  I  V  T  N  W  L  A  K  V  N  T  Q  I  D  L  I  R  K  K  M  K
3361 GATGAGGTGTATAAGTATATTGTTACCAACTGGCTCGCTAAAGTAAACACCCAGATTGACCTGATTCGCAAGAAGATGAA 3440

E  A  L  E  N  Q  A  E  A  T  K  A  I  I  N  Y  Q  Y  N  Q  Y  T  E  E  E  K  N
3441 AGAAGCGCTGGAAAACCAAGCAGAAGCGACCAAAGCTATTATCAACTATCAATATAACCAGTACACAGAGGAAGAAAAGA 3520

N  I  N  F  N  I  D  D  L  S  S  K  L  N  E  S  I  N  K  A  M  I  N  I  N  K
3521 ATAACATCAACTTCAACATCGACGACTTATCTTCAAAGCTGAATGAATCTATTAACAAAGCGATGATTAATATTAACAAG 3600

F  L  N  Q  C  S  V  S  Y  L  M  N  S  M  I  P  Y  G  V  K  R  L  E  D  F  D  A
3601 TTCTTGAACCAATGTAGTGTCAGCTATCTGATGAACTCGATGATCCCATATGGTGTGAAACGTCTGGAAGACTTCGATGC 3680

S  L  K  D  A  L  L  K  Y  I  Y  D  N  R  G  T  L  I  G  Q  V  D  R  L  K  D  K
3681 AAGCCTTAAAGATGCCCTTCTGAAGTATATTTACGATAATCGCGGAACTCTTATTGGCCAAGTGGATCGCTTAAAAGATA 3760

V  N  N  T  L  S  T  D  I  P  F  Q  L  S  K  Y  V  D  N  Q  R  L  L  S  T  F
3761 AAGTCAACAACACGCTGAGTACAGACATCCCTTTTCAGCTGTCTAAATATGTGGACAATCAGCGCCTGCTGTCCACGTTT 3840

T  E  Y  I  K  N  I  I  N  T  S  I  L  N  L  R  Y  E  S  N  H  L  I  D  L  S  R
3841 ACGGAATACATCAAAAACATCATCAACACTAGTATTCTGAACTTGCGTTACGAGAGTAACCATCTGATTGATCTGAGCCG 3920

Y  A  S  K  I  N  I  G  S  K  V  N  F  D  P  I  D  K  N  Q  I  Q  L  F  N  L  E
3921 TTACGCATCTAAAATCAACATCGGCTCGAAGGTGAACTTCGATCCTATCGACAAAAACCAGATTCAATTGTTCAACTTAG 4000

S  S  K  I  E  V  I  L  K  N  A  I  V  Y  N  S  M  Y  E  N  F  S  T  S  F  W
4001 AATCGTCAAAGATTGAAGTTATCTTAAAAAATGCGATTGTATATAATTCAATGTACGAAAATTTCTCTACGAGCTTTGG 4080

I  R  I  P  K  Y  F  N  S  I  S  L  N  N  E  Y  T  I  I  N  C  M  E  N  N  S  G
4081 ATTCGTATTCCGAAATATTTCAACAGTATCTCTTTAAACAACGAGTATACTATCATCAATTGTATGGAGAATAACAGCGG 4160

W  K  V  S  L  N  Y  G  E  I  I  W  T  L  Q  D  T  Q  E  I  K  Q  R  V  V  F  K
4161 GTGGAAAGTGAGCCTTAACTATGGTGAAATCATCTGGACTCTGCAGGACACTCAAGAAATTAAACAACGCGTGGTGTTTA 4240

Y  S  Q  M  I  N  I  S  D  Y  I  N  R  W  I  F  V  T  I  T  N  N  R  L  N  N
4241 AATACTCACAGATGATTAACATCTCGGATTATATTAATCGCTGGATTTTTGTGACAATTACTAACAACCGGCTGAACAAC 4320

S  K  I  Y  I  N  G  R  L  I  D  Q  K  P  I  S  N  L  G  N  I  H  A  S  N  N  I
4321 AGCAAAATTTACATTAACGGTCGCCTGATCGATCAGAAACCAATCAGTAATCTCGGTAACATTCACGCATCGAATAATAT 4400

M  F  K  L  D  G  C  R  D  T  H  R  Y  I  W  I  K  Y  F  N  L  F  D  K  E  L  N
4401 CATGTTCAAACTGGATGGTTGTCGCGACACGCACCGTTACATTTGGATCAAATACTTCAATTTATTCGACAAAGAACTCA 4480

E  K  E  I  K  D  L  Y  D  N  Q  S  N  S  G  I  L  K  D  F  W  G  D  Y  L  Q
4481 ACGAAAAGGAGATTAAGGATCTTTATGACAATCAGTCTAATTCGGGTATTCTGAAAGACTTTTGGGGTGATTACCTTCAG 4560

Y  D  K  P  Y  Y  M  L  N  L  Y  D  P  N  K  Y  V  D  V  N  N  V  G  I  R  G  Y
4561 TACGATAAACCGTATTATATGTTAAACTTATATGATCCGAATAAATACGTTGACGTCAACAACGTTGGCATTCGTGGCTA 4640

M  Y  L  K  G  P  R  G  S  V  M  T  T  N  I  Y  L  N  S  S  L  Y  R  G  T  K  F
4641 TATGTATCTGAAAGGGCCGCGTGGCAGCGTGATGACCACTAACATTTACTTAAACTCCTCCCTCTATCGCGGTACTAAAT 4720

I  I  K  K  Y  A  S  G  N  K  D  N  I  V  R  N  N  D  R  V  Y  I  N  V  V  V
4721 TTATTATCAAGAAATATGCCTCTGGCAACAAGGACAATATCGTACGCAATAACGATCGCGTCTACATTAACGTGGTGGTG 4800

K  N  K  E  Y  R  L  A  T  N  A  S  Q  A  G  V  E  K  I  L  S  A  L  E  I  P  D
4801 AAGAATAAAGAATATCGTCTGGCGACCAATGCTAGTCAGGCGGGCGTGGAGAAAATTCTGTCTGCACTTGAAATCCCGGA 4880

V  G  N  L  S  Q  V  V  V  M  K  S  K  N  D  Q  G  I  T  N  K  C  K  M  N  L  Q
4881 TGTGGGTAATTTATCCCAGGTGGTTGTGATGAAAAGTAAAAATGACCAAGGGATCACCAATAAATGCAAAATGAATCTGC 4960

D  N  N  G  N  D  I  G  F  I  G  F  H  Q  F  N  N  I  A  K  L  V  A  S  N  W
4961 AAGATAACAACGGCAACGACATTGGTTTTATCGGCTTCCACCAATTCAATAATATCGCGAAACTGGTGGCCTCAAATTGG 5040

Y  N  R  Q  I  E  R  S  S  R  T  L  G  C  S  W  E  F  I  P  V  D  D  G  W  G  E
5041 TACAACCGTCAGATTGAGCGCAGCTCCCGCACTTTAGGCTGTAGCTGGGAGTTCATTCCGGTAGATGACGGTTGGGGAGA 5120
```

Thrombin cleavage site
↓

```
        R  P  L  K  V  D  K  L  L  V  P  R  G  S  K  L  Q  L  E  H  H  H  H  H  H  *
5121 ACGCCCATTGAAAGTCGACAAGCTTCTGGTACCGCGCGGCAGCAAACTGCAGCTCGAGCACCACCACCACCACCACTGA 5199
```

This example of the present invention addresses at least two major problems presented by the state of the art. Firstly, it provides a long-lasting BoNT chimera which has broadened anti-nociceptive therapeutic potential. Secondly, it provides a long-lasting BoNT-derived therapeutic with unique potential for chronic pain therapy.

Management of chronic pain poses a major challenge for modern healthcare because sufferers represent over 20% of the adult population. A substantial proportion of the population do not respond to the commonly-used pain killers. Additionally, the increase in drug dependence and abuse linked to the profusion of prescription opiates, and the short half-lives of many analgesics in most cases originally prescribed for pain, makes the use of opioids and non-steroid anti-inflammatory drugs unattractive options.

Therapeutic uses of BoNT/A complex proved beneficial for some but not all migraine sufferers, due to a postulated interference with pain pathways. The failure of BoNT/A to attenuate neuronal firing elicited by a pain peptide or TRPV1 activation of C-fibres in situ and inability to block CGRP release from cultured neurons highlight that it is essential to develop long-lasting and more-widely effective forms.

A BoNT-derivative chimera of BoNT/A and BoNT/E enters TGNs successfully, and gives/E-like SNAP-25 cleavage products which, in turn, inhibits the release of pain mediators; however, its short duration of action limits clinical applications.

The present invention combines domains of at least two BoNTs of different serotypes together to produce novel therapeutics. This innovative strategy can be used to generate other chimeric multichain therapeutics, including constructs comprising multiple LCs from different BoNT serotypes to yield therapeutics having desired properties; for example, a multi-SNARE-cleaving toxin (cleaving different SNARE proteins) therapeutic, which can be constructed, for example, by attaching LC/C1 to BoNT/A instead of LC/E.

Example 9

In another example, a multi-endopeptidase construct was created by substituting the LC/E gene in LC/E-BoNT/A nucleic acid with a synthetic LC/B gene to create a final plasmid encoding LC/B-BoNT/A as a single open reading frame in a manner substantially similar to that described above.

For expression of LC/B-BoNT/A, the sequence-verified nucleic construct was transformed into *E. coli* strain BL21 (DE3), and the resultant protein was expressed as described previously for LC/E-BoNT/A. Partial purification of the $His_6$-tagged toxin from the cleared bacteria lysate was achieved using an IMAC affinity separation step, using Talon superflow resin. A major protein of Mr~200 k was eluted by ≥150 mM imidazole; this is demonstrated in FIG. 8B, which shows SDS-PAGE under reducing conditions and Coomassie blue staining of the gel. Gel lanes are as follows: Lanes 1: cleared lysate before application to IMAC column; 2: the IMAC column flowthrough fraction; 3: the IMAC column wash fraction; 4-8, fractions eluted using imidazole.

The pooled IMAC eluate was buffer-exchanged into 25 mM HEPES/145 mM NaCl (pH 7.4) and aliquots analysed by SDS-PAGE. FIG. 8C shows SDS-PAGE of the purified protein in which aliquots were electrophoresed under reducing (+) and non-reducing (−). Electrophoresis confirmed that the protein was indeed expressed in a single-chain ("SC") form, as revealed by a major band migrating with an apparent molecular weight of about 200 kDa. This band was seen in either the absence or presence of reducing agent. See e.g., lanes SC (−) and SC (+) of the Coomassie Brilliant Blue-stained gel in FIG. 8C.

Nicking of this single chain protein (and removal of the $His_6$ tag) was achieved by incubation of the protein with biotinylated thrombin (1 unit/mg of toxin) at 22° C. for 3 h; the thrombin protease is then removed by treating the sample with streptavidin immobilized on agarose. Two bands (not well resolved by SDS-PAGE due to the similarity in mobility of the two protein chains) having apparent molecular weight of about 100 K appear after thrombin treatment of the protein in samples run on an SDS-PAGE gel under reducing conditions; the ~200 K band is not seen under these conditions, but is present in gels run under non-reducing conditions, while the ~100 KDa bands are absent in these latter samples. See e.g., lanes DC (−) and DC (+) of the Coomassie Brilliant Blue-stained gel in FIG. 8C. The ~100 K bands are believed to represent both the LC/B-LC/A and the HC/A chains, which have small difference in sizes.

Rat cultured cerebellar granule neurons (CGNs) were incubated with the thrombin-treated LC/B-BoNT/A at 5-fold serially diluted concentrations from 0.32 μM to 5000 μM. After 24 hours' incubation at 37° C. with LC/B-BoNT/A, cells were then harvested and subjected to SDS-PAGE and Western blotting, using a) an anti-SNAP-25 antibody recognising both intact SNAP-25 and the large cleavage product of treatment with LC/A, and b) an anti-VAMP2 antibody picking up the intact version. An anti-syntaxin 1 antibody was used to detect the SNARE protein syntaxin 1, which was used as a positive internal loading control. Representative Western blot(FIG. 8D) and quantitative data (FIG. 8E) from multiple blots show that LC/B-BoNT/A cleaved SNAP-25 as well as VAMP2; however, the VAMP2 was cleaved effectively at higher concentrations of the LC/B-BoNT/A. While not wishing to be limited by theory, this result may arise from sequestration of the composite toxin to the membrane through the LC of BoNT/A that would lower VAMP cleavage [Fernández-Salas et al, Proc. Natt. Acad. Sci. USA. 2004, 101(9):3208-3213].

Example 10

As illustrated by the positive functional results from LC/E-BoNT/A (two active proteases recognising two different sequences of same substrate) and LC/B-BoNT/A (two proteases cleaving two different substrates), and in view of the disclosure of this patent application, one of ordinary skill in the art will be aware that additional examples of the present invention may involve compositions and methods for creating various other multi-endopeptidase therapeutics by combination of different Clostridial neurotoxins or Clostridial neurotoxin subtypes for inhibiting the release of pain-peptides and neurotransmitters from various nerve types (eg. sensory and sympathetic neurons). Moreover, the activity of the multi-endopeptidase toxin would indirectly block the activation by such mediators of cytokine-releasing cells.

For example, a single therapeutic which inactivates all three SNARE proteins is created by recombinant fusion of the light chain of BoNT/D (LC/D) to the N-terminus of BoNT/C1 via a linker (see FIG. 9). Briefly, a nucleic acid encoding the LC/D endopeptidase is inserted "in-frame" in LC/E-BoNT/A to replace LC/E. The synthetic gene encoding LC/D is designed to have codons optimised for optimal expression in *E. coli*. The resultant plasmid encodes an intermediate protein comprising LC/D-BoNT/A.

Subsequently, a synthetic gene encoding BoNT/C1 (like the BoNT/A construct, with a thrombin cleavage site in its loop region) is used to replace the BoNT/A gene in LC/D-BoNT/A to yield a final nucleic acid construct comprising an LC/D-BoNT/C1 open reading frame. The expressed, purified and nicked LC/D-BoNT/C1 therapeutic will have ability to inactive VAMP 1-3 by cleavage with LC/D; the LC/C1 protease will cleave syntaxin 1-3 and SNAP-25. This molecule will be suitable for the treatment of chronic inflammatory and neuropathic pain.

Example 11

A 60 year-old man presents with severe chronic joint pain in the left hip, and has difficulty walking. Following examination, the patient is diagnosed with rheumatoid arthritis of the acetabulofemoral (hip) joint.

The patient is administered the Clostridial neurotoxin derivative LC/E-BoNT/A an effective dose by injection directly into both the femoral ganglion and the sciatic ganglion. The gene construct is made as described above and the Clostridial toxin derivative is affinity purified following the expression thereof using the $His_6$ tag (SEQ ID NO: 15), following by ion exchange chromatography and thrombin nicking before use.

Within 48 hours, there is notable improvement in the extent and acuteness of pain, and within one week the patient is able to walk with little difficulty.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention. Each and every feature described herein, and each and every combination of two or more of such features, is included within the scope of the present invention provided that the features included in such a combination are not mutually inconsistent. Furthermore, any composition or apparatus of the invention will be understood to comprise, consist essentially of, or consist of one or more element of the claim, and additionally, each and every element not specifically included as an element of a claim shall be considered to have basis herein to be specifically excluded in a negative limitation from that claim.

Any and all patents, publications, patent applications, and nucleotide and/or amino acid sequences referred to by accession numbers cited in this specification are hereby incorporated by reference as part of this specification in its entirety.

We claim:

1. A nucleic acid having a nucleotide sequence encoding a polypeptide having a *Clostridium botulinum* translocation activity, a *Clostridium botulinum* cell surface binding activity, a first *Clostridium botulinum* endopeptidase activity and a second *Clostridium botulinum* endopeptidase activity said nucleic acid sequence being derived from a *Clostridium botulinum* nucleotide sequence and comprising a single open reading frame encoding, in sequence from carboxy terminus to amino terminus:
   a) a *Clostridium botulinum*-derived binding domain comprising an $H_{CN}$ subdomain and an $H_{CC}$ subdomain,
   b) a *Clostridium botulinum*-derived translocation domain,
   c) a *Clostridium botulinum*-derived first endopeptidase domain,
   d) and a *Clostridium botulinum*-derived second endopeptidase domain different from said first endopeptidase domain, wherein, upon expression, each of said first endopeptidase domain and said second endopeptidase domain has a different selective proteolytic activity against a SNARE protein, and wherein said first and second domains endopeptidase are proteolytically active and recognize different amino acid cleavage sites in a SNARE protein.

2. The nucleic acid of claim 1 wherein codons encoding each of the binding domain, the translocation domain, the first endopeptidase domain, and the second endopeptidase domain, are optimized for expression in a cell type selected from the group consisting of: a bacterial cell, a mammalian cell, a yeast cell and an insect cell.

3. The nucleic acid of claim 2 wherein the codons are optimized for expression in an *E. coli* bacterial cell.

4. The nucleic acid of claim 1 wherein at least two domains selected from the group consisting of the binding domain, the translocation domain, the first endopeptidase domain, and the second endopeptidase domain are encoded by nucleic acid sequences derived from different Clostridial neurotoxins or Clostridial neurotoxin subtypes selected from the group consisting of: BoNT/A, BoNT/B, BoNT/C1, BoNT/D, BoNT/E, BoNT/F, and BoNT/G.

5. The nucleic acid of claim 4 wherein the first endopeptidase domain and the second endopeptidase domain are encoded by nucleic acid sequences derived from different Clostridial neurotoxin or Clostridial neurotoxin subtypes independently selected from the group consisting of: BoNT/A, BoNT/B, BoNT/C1, BoNT/D, BoNT/E, BoNT/F, and BoNT/G.

6. The nucleic acid of claim 5 wherein the first endopeptidase domain is encoded by nucleic acid sequences derived from BoNT/A and said second endopeptidase domain is encoded by nucleic acid sequences derived from BoNT/C1.

7. The nucleic acid of claim 5 wherein the first endopeptidase domain is encoded by nucleic acid sequences derived from BoNT/A and said second endopeptidase domain is encoded by nucleic acid sequences derived from BoNT/E.

8. The nucleic acid of claim 7 wherein said open reading frame encodes at least six contiguous histidine residues located between the nucleotide sequence encoding said binding domain and the stop codon.

9. A nucleic acid having a nucleotide sequence encoding a polypeptide comprising a consisting of a *Clostridium botulinum*-derived neurotoxin, said nucleic acid sequence comprising a single open reading frame encoding, in sequence from carboxy terminus to amino terminus:
   a) a binding domain comprising an $H_{CN}$ subdomain and an $H_{CC}$ subdomain,
   b) a translocation domain,
   c) a first endopeptidase domain,
   d) and a second endopeptidase domain different from said first endopeptidase domain, wherein, upon translation of said nucleic acid, said neurotoxin has greater analgesic activity against chronic pain than an otherwise identical neurotoxin in which one of said first or second endopeptidase is inactive as a protease.

10. The nucleic acid of claim 9 encoding a protease cleavage site located at a position between those regions encoding the translocation domain and the first endopeptidase domain.

11. The nucleic acid of claim 9 wherein each of said first endopeptidase domain and said second endopeptidase domain has a selective proteolytic activity against the SNARE protein SNAP-25, and recognizes a different amino acid cleavage site in SNAP-25.

12. The nucleic acid of claim 9 wherein the binding domain encoded by said nucleic acid comprises a BoNT neurotoxin Hc region.

13. The nucleic acid of claim 9 wherein the binding domain encoded by said nucleic acid lacks a complete BoNT neurotoxin Hc region.

14. The nucleic acid of claim 13 wherein the binding domain encoded by said nucleic acid comprises a functional BoNT $H_{CN}$ region.

15. The nucleic acid of claim 9 wherein the binding domain encoded by said nucleic acid comprises a non-Clostridial binding moiety.

16. The nucleic acid of claim 15 wherein the binding domain encoded by said nucleic acid comprises a BoNT neurotoxin Hc region.

17. The nucleic acid of claim 15 wherein the binding domain encoded by said nucleic acid lacks a complete neurotoxin BoNT Hc region.

18. The nucleic acid of claim 17 wherein the binding domain encoded by said nucleic acid comprises a functional BoNT $H_{CN}$ region.

19. The nucleic acid of claim 9 wherein the first endopeptidase domain and said second endopeptidase domain encoded by said nucleic acid are derived from different Clostridial neurotoxins and said first endopeptidase and said second endopeptidase are independently selected from the group consisting of an endopeptidase derived from: BoNT/A, BoNT/B, BoNT/C1, BoNT/D, BoNT/E, BoNT/F, BoNT/G.

20. The nucleic acid of claim 9 wherein the binding domain comprises a BoNT binding subdomain $H_{CN}$ and a binding subdomain $H_{CC}$, and wherein binding subdomain $H_{CN}$, binding subdomain $H_{CC}$, and said translocation domain encoded by the nucleic acid are respectively independently derived from a naturally occurring BoNT binding subdomain $H_{CN}$, a naturally occurring BoNT binding subdomain $H_{CC}$, and a naturally occurring BoNT translocation domain, each from a Clostridial neurotoxin subtype selected from the group consisting of BoNT/A, BoNT/B, BoNT/C1, BoNT/D, BoNT/E, BoNT/F, BoNT/G.

* * * * *

SEQUENCE LISTING

```
<160> NUMBER OF SEQ ID NOS: 15

<210> SEQ ID NO 1
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(78)

<400> SEQUENCE: 1 tgt gtc cgc ggt att atc acc agc aaa acc aaa tcc ttg gtg ccc cgc      48
Cys Val Arg Gly Ile Ile Thr Ser Lys Thr Lys Ser Leu Val Pro Arg
1               5                   10                  15 ggc tct aac aag gcg ctc aat gat tta tgc                              78
Gly Ser Asn Lys Ala Leu Asn Asp Leu Cys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Val Arg Gly Ile Ile Thr Ser Lys Thr Lys Ser Leu Val Pro Arg
1               5                   10                  15

Gly Ser Asn Lys Ala Leu Asn Asp Leu Cys
            20                  25

<210> SEQ ID NO 3
<211> LENGTH: 69
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: CDS
<222> LOCATION: (1)..(66)

<400> SEQUENCE: 3

```
aaa gtc gac aag ctt ctg gta ccg cgc ggc agc aaa ctg cag ctc gag      48
Lys Val Asp Lys Leu Leu Val Pro Arg Gly Ser Lys Leu Gln Leu Glu
1               5                   10                  15 cac cac cac cac cac cac tga                                          69
His His His His His His
            20
```

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Lys Val Asp Lys Leu Leu Val Pro Arg Gly Ser Lys Leu Gln Leu Glu
1               5                   10                  15

His His His His His His
            20
```

<210> SEQ ID NO 5
<211> LENGTH: 5199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(5196)

<400> SEQUENCE: 5

```
atg cct aaa atc aat tcg ttc aac tat aat gac ccg gtt aac gat cgc      48
Met Pro Lys Ile Asn Ser Phe Asn Tyr Asn Asp Pro Val Asn Asp Arg
1               5                   10                  15 acg atc ctg tat atc aag cca ggt gga tgt caa gaa ttt tat aaa tca      96
Thr Ile Leu Tyr Ile Lys Pro Gly Gly Cys Gln Glu Phe Tyr Lys Ser
            20                  25                  30 ttc aac atc atg aaa aat att tgg att atc ccg gaa cgc aac gtg atc     144
Phe Asn Ile Met Lys Asn Ile Trp Ile Ile Pro Glu Arg Asn Val Ile
        35                  40                  45 ggc acg acg cct caa gat ttt cac ccg ccg acc tcc ctg aaa aat ggc     192
Gly Thr Thr Pro Gln Asp Phe His Pro Pro Thr Ser Leu Lys Asn Gly
    50                  55                  60 gac agt tcc tac tat gac ccg aat tat tta caa tcg gat gaa gaa aaa     240
Asp Ser Ser Tyr Tyr Asp Pro Asn Tyr Leu Gln Ser Asp Glu Glu Lys
65                  70                  75                  80 gat cgt ttc ctc aag atc gtc acg aaa att ttc aac cgc atc aat aac     288
Asp Arg Phe Leu Lys Ile Val Thr Lys Ile Phe Asn Arg Ile Asn Asn
                85                  90                  95 aat ctg tcc ggt ggc atc tta ctt gag gaa tta tct aaa gct aat ccg     336
Asn Leu Ser Gly Gly Ile Leu Leu Glu Glu Leu Ser Lys Ala Asn Pro
            100                 105                 110 tat ctg ggg aac gat aat acc ccg gat aat cag ttc cac att ggc gat     384
Tyr Leu Gly Asn Asp Asn Thr Pro Asp Asn Gln Phe His Ile Gly Asp
        115                 120                 125
```

-continued

| | | |
|---|---|---|
| gcg agc gct gtg gaa att aaa ttc agc aac ggc agt caa gat att ctt<br>Ala Ser Ala Val Glu Ile Lys Phe Ser Asn Gly Ser Gln Asp Ile Leu<br>130                     135                     140 | 432 | |
| ctc cca aac gtg att atc atg ggg gct gaa cct gat ctt ttc gaa act<br>Leu Pro Asn Val Ile Ile Met Gly Ala Glu Pro Asp Leu Phe Glu Thr<br>145                     150                  155              160 | 480 | |
| aat agt tcc aat att tca ctg cgc aat aat tat atg ccg tcg aac cat<br>Asn Ser Ser Asn Ile Ser Leu Arg Asn Asn Tyr Met Pro Ser Asn His<br>               165                  170                  175 | 528 | |
| ggc ttt ggc tca atc gca att gtg acg ttc tca cct gaa tat agt ttt<br>Gly Phe Gly Ser Ile Ala Ile Val Thr Phe Ser Pro Glu Tyr Ser Phe<br>              180                  185                  190 | 576 | |
| cgt ttt aac gac aac agc atg aat gaa ttt atc caa gac ccg gcg ctg<br>Arg Phe Asn Asp Asn Ser Met Asn Glu Phe Ile Gln Asp Pro Ala Leu<br>               195                  200                205 | 624 | |
| act ttg atg cat gaa ctg atc cat agc ttg cac ggc ctg tat ggc gct<br>Thr Leu Met His Glu Leu Ile His Ser Leu His Gly Leu Tyr Gly Ala<br>210                     215                  220 | 672 | |
| aaa ggc atc act acc aaa tac acg att acg caa aaa caa aat ccc tta<br>Lys Gly Ile Thr Thr Lys Tyr Thr Ile Thr Gln Lys Gln Asn Pro Leu<br>225                     230                  235              240 | 720 | |
| atc acc aac atc cgc ggc acc aac att gaa gaa ttt ctg acc ttc ggc<br>Ile Thr Asn Ile Arg Gly Thr Asn Ile Glu Glu Phe Leu Thr Phe Gly<br>               245                  250                255 | 768 | |
| gga acg gat ctg aac atc att aca tct gcc caa agc aac gac atc tat<br>Gly Thr Asp Leu Asn Ile Ile Thr Ser Ala Gln Ser Asn Asp Ile Tyr<br>              260                  265                  270 | 816 | |
| acc aat ctg tta gca gat tat aag aaa atc gcc agc aaa tta tct aaa<br>Thr Asn Leu Leu Ala Asp Tyr Lys Lys Ile Ala Ser Lys Leu Ser Lys<br>             275                  280                285 | 864 | |
| gtt cag gtc agc aat ccg ctg tta aac ccg tat aaa gat gtg ttc gaa<br>Val Gln Val Ser Asn Pro Leu Leu Asn Pro Tyr Lys Asp Val Phe Glu<br>290                     295                  300 | 912 | |
| gcg aaa tac ggc ttg gac aaa gac gct agt ggc atc tat tcc gtc aat<br>Ala Lys Tyr Gly Leu Asp Lys Asp Ala Ser Gly Ile Tyr Ser Val Asn<br>305                     310                  315              320 | 960 | |
| att aat aaa ttt aac gat att ttc aaa aaa tta tat tcc ttc acc gaa<br>Ile Asn Lys Phe Asn Asp Ile Phe Lys Lys Leu Tyr Ser Phe Thr Glu<br>               325                  330                335 | 1008 | |
| ttt gat ttg gcc acc aaa ttc cag gtc aaa tgt cgt caa acc tat att<br>Phe Asp Leu Ala Thr Lys Phe Gln Val Lys Cys Arg Gln Thr Tyr Ile<br>              340                  345                  350 | 1056 | |
| ggc caa tac aaa tat ttt aaa ctg agc aac ctg ctt aat gat tcc atc<br>Gly Gln Tyr Lys Tyr Phe Lys Leu Ser Asn Leu Leu Asn Asp Ser Ile<br>             355                  360                365 | 1104 | |
| tac aat att agt gaa ggt tac aat att aat aac ctg aaa gtt aac ttt<br>Tyr Asn Ile Ser Glu Gly Tyr Asn Ile Asn Asn Leu Lys Val Asn Phe<br>370                     375                  380 | 1152 | |
| cgt ggg caa aat gcg aat ctg aac ccc cgc atc att aca ccc atc acg<br>Arg Gly Gln Asn Ala Asn Leu Asn Pro Arg Ile Ile Thr Pro Ile Thr<br>385                     390                  395              400 | 1200 | |
| ggc cgt ggg ttg gtc aaa aaa att att cgc ttt gat atc atg ccg ttc<br>Gly Arg Gly Leu Val Lys Lys Ile Ile Arg Phe Asp Ile Met Pro Phe<br>               405                  410                415 | 1248 | |
| gta aac aaa cag ttc aac tat aaa gac cca gtc aac ggc gtg gac att<br>Val Asn Lys Gln Phe Asn Tyr Lys Asp Pro Val Asn Gly Val Asp Ile<br>              420                  425                430 | 1296 | |
| gcc tat atc aaa atc ccg aat gcg ggt caa atg cag ccc gtg aaa gca<br>Ala Tyr Ile Lys Ile Pro Asn Ala Gly Gln Met Gln Pro Val Lys Ala<br>              435                  440                445 | 1344 | |

```
ttt aaa atc cat aac aaa att tgg gtg atc ccg gag cgc gat acg ttc    1392
Phe Lys Ile His Asn Lys Ile Trp Val Ile Pro Glu Arg Asp Thr Phe
    450                 455                 460 acg aac ccg gaa gaa gga gat tta aac cca ccg cct gag gct aaa cag    1440
Thr Asn Pro Glu Glu Gly Asp Leu Asn Pro Pro Pro Glu Ala Lys Gln
465                 470                 475                 480 gtc ccg gtg tct tac tat gat agc aca tac ctg agt acc gac aat gaa    1488
Val Pro Val Ser Tyr Tyr Asp Ser Thr Tyr Leu Ser Thr Asp Asn Glu
                    485                 490                 495 aag gac aac tac ctg aaa ggt gtt acc aaa ctg ttc gag cgc att tat    1536
Lys Asp Asn Tyr Leu Lys Gly Val Thr Lys Leu Phe Glu Arg Ile Tyr
                500                 505                 510 tcg aca gat ctc ggt cgc atg ttg ctg act tct att gtg cgc ggc att    1584
Ser Thr Asp Leu Gly Arg Met Leu Leu Thr Ser Ile Val Arg Gly Ile
            515                 520                 525 ccg ttt tgg ggt ggt agc acc atc gat aca gaa ctc aaa gtg att gac    1632
Pro Phe Trp Gly Gly Ser Thr Ile Asp Thr Glu Leu Lys Val Ile Asp
        530                 535                 540 acc aac tgc atc aat gtg att cag cct gat ggg agc tac cgg tcc gaa    1680
Thr Asn Cys Ile Asn Val Ile Gln Pro Asp Gly Ser Tyr Arg Ser Glu
545                 550                 555                 560 gag ctt aac ctc gta atc att ggc ccg agc gcg gat att atc caa ttc    1728
Glu Leu Asn Leu Val Ile Ile Gly Pro Ser Ala Asp Ile Ile Gln Phe
                    565                 570                 575 gaa tgt aaa tct ttt ggg cat gaa gtc ctg aat ctg acg cgg aat ggc    1776
Glu Cys Lys Ser Phe Gly His Glu Val Leu Asn Leu Thr Arg Asn Gly
                580                 585                 590 tat gga tcg acg cag tat att cgt ttt tct cca gat ttc aca ttt gga    1824
Tyr Gly Ser Thr Gln Tyr Ile Arg Phe Ser Pro Asp Phe Thr Phe Gly
            595                 600                 605 ttt gaa gaa agc ctc gaa gtt gat acg aac cct ctt tta ggc gcg gga    1872
Phe Glu Glu Ser Leu Glu Val Asp Thr Asn Pro Leu Leu Gly Ala Gly
        610                 615                 620 aaa ttc gcg acg gac cca gcg gtg acc ttg gca cat gaa ctt att cat    1920
Lys Phe Ala Thr Asp Pro Ala Val Thr Leu Ala His Glu Leu Ile His
625                 630                 635                 640 gcc ggg cat cgc ttg tat gga atc gcc att aac ccg aac cgt gtt ttc    1968
Ala Gly His Arg Leu Tyr Gly Ile Ala Ile Asn Pro Asn Arg Val Phe
                    645                 650                 655 aag gtg aat acg aac gcg tat tac gag atg tcg ggc tta gaa gtg tcc    2016
Lys Val Asn Thr Asn Ala Tyr Tyr Glu Met Ser Gly Leu Glu Val Ser
                660                 665                 670 ttt gaa gaa ctg cgc acg ttt ggc ggt cat gat gca aaa ttt att gat    2064
Phe Glu Glu Leu Arg Thr Phe Gly Gly His Asp Ala Lys Phe Ile Asp
            675                 680                 685 agt ctg caa gaa aac gaa ttt cgg ctg tac tat tac aat aaa ttc aaa    2112
Ser Leu Gln Glu Asn Glu Phe Arg Leu Tyr Tyr Tyr Asn Lys Phe Lys
        690                 695                 700 gac att gca tca acc tta aac aag gcg aaa agc att gtg ggt acc acg    2160
Asp Ile Ala Ser Thr Leu Asn Lys Ala Lys Ser Ile Val Gly Thr Thr
705                 710                 715                 720 gct agc tta caa tat atg aaa aac gtt ttc aaa gaa aaa tac ctc ctt    2208
Ala Ser Leu Gln Tyr Met Lys Asn Val Phe Lys Glu Lys Tyr Leu Leu
                    725                 730                 735 agc gaa gac act tcc ggc aaa ttc tct gtc gat aaa ctg aaa ttt gat    2256
Ser Glu Asp Thr Ser Gly Lys Phe Ser Val Asp Lys Leu Lys Phe Asp
                740                 745                 750 aaa ctg tat aaa atg ctc acc gag atc tac aca gag gat aac ttt gtc    2304
Lys Leu Tyr Lys Met Leu Thr Glu Ile Tyr Thr Glu Asp Asn Phe Val
```

-continued

|  |  |  |  |
|---|---|---|---|
| 755 | 760 | 765 | |

| aaa ttc ttc aag gtc ttg aat cgg aaa acc tat ctg aac ttc gat aaa<br>Lys Phe Phe Lys Val Leu Asn Arg Lys Thr Tyr Leu Asn Phe Asp Lys<br>770                    775                    780 | 2352 |
| gcc gtc ttt aag atc aac atc gta ccg aaa gtt aac tac acc atc tat<br>Ala Val Phe Lys Ile Asn Ile Val Pro Lys Val Asn Tyr Thr Ile Tyr<br>785                    790                    795                    800 | 2400 |
| gat ggc ttt aat ctg cgc aat acg aat ctg gcg gcg aac ttt aac ggc<br>Asp Gly Phe Asn Leu Arg Asn Thr Asn Leu Ala Ala Asn Phe Asn Gly<br>                    805                    810                    815 | 2448 |
| cag aac acc gaa atc aac aac atg aac ttt act aaa ctg aaa aat ttt<br>Gln Asn Thr Glu Ile Asn Asn Met Asn Phe Thr Lys Leu Lys Asn Phe<br>820                    825                    830 | 2496 |
| acc ggc ttg ttt gaa ttt tat aag ctc ctg tgt gtc cgc ggt att atc<br>Thr Gly Leu Phe Glu Phe Tyr Lys Leu Leu Cys Val Arg Gly Ile Ile<br>                    835                    840                    845 | 2544 |
| acc agc aaa acc aaa tcc ttg gtg ccc cgc ggc tct aac aag gcg ctc<br>Thr Ser Lys Thr Lys Ser Leu Val Pro Arg Gly Ser Asn Lys Ala Leu<br>850                    855                    860 | 2592 |
| aat gat tta tgc atc aag gtg aac aac tgg gac ttg ttt ttc tct cca<br>Asn Asp Leu Cys Ile Lys Val Asn Asn Trp Asp Leu Phe Phe Ser Pro<br>865                    870                    875                    880 | 2640 |
| tct gaa gat aat ttt act aac gac ttg aac aaa gga gag gaa att act<br>Ser Glu Asp Asn Phe Thr Asn Asp Leu Asn Lys Gly Glu Glu Ile Thr<br>                    885                    890                    895 | 2688 |
| tcc gat acc aac atc gaa gca gcg gaa gag aat att agc ctg gat ctt<br>Ser Asp Thr Asn Ile Glu Ala Ala Glu Glu Asn Ile Ser Leu Asp Leu<br>900                    905                    910 | 2736 |
| att caa caa tat tac ctg acc ttt aat ttt gat aac gag cct gag aac<br>Ile Gln Gln Tyr Tyr Leu Thr Phe Asn Phe Asp Asn Glu Pro Glu Asn<br>                    915                    920                    925 | 2784 |
| att tcc att gag aat ctc agc tct gac atc atc ggc cag ctg gaa ctg<br>Ile Ser Ile Glu Asn Leu Ser Ser Asp Ile Ile Gly Gln Leu Glu Leu<br>930                    935                    940 | 2832 |
| atg ccg aat atc gaa cgc ttt cct aat gga aag aaa tat gaa ttg gac<br>Met Pro Asn Ile Glu Arg Phe Pro Asn Gly Lys Lys Tyr Glu Leu Asp<br>945                    950                    955                    960 | 2880 |
| aaa tac acc atg ttc cac tat ctc cgc gcg cag gag ttt gag cac ggc<br>Lys Tyr Thr Met Phe His Tyr Leu Arg Ala Gln Glu Phe Glu His Gly<br>                    965                    970                    975 | 2928 |
| aag tct cgt att gct ctg acc aat tcg gta aac gaa gcc ctt tta aat<br>Lys Ser Arg Ile Ala Leu Thr Asn Ser Val Asn Glu Ala Leu Leu Asn<br>                    980                    985                    990 | 2976 |
| cct tcg cgt gtg tac acc ttt ttc tca agc gat tat gtt aaa aaa gtg<br>Pro Ser Arg Val Tyr Thr Phe Phe Ser Ser Asp Tyr Val Lys Lys Val<br>                    995                    1000                  1005 | 3024 |
| aac aag gcg acc gaa gcg gcg atg ttt ttg gga tgg gtg gaa caa<br>Asn Lys Ala Thr Glu Ala Ala Met Phe Leu Gly Trp Val Glu Gln<br>1010                    1015                    1020 | 3069 |
| ctg gta tat gac ttt acg gat gaa act tct gaa gtc tcg acc acc<br>Leu Val Tyr Asp Phe Thr Asp Glu Thr Ser Glu Val Ser Thr Thr<br>1025                    1030                    1035 | 3114 |
| gac aaa att gcc gat att acc att atc att ccc tat att ggc cct<br>Asp Lys Ile Ala Asp Ile Thr Ile Ile Ile Pro Tyr Ile Gly Pro<br>1040                    1045                    1050 | 3159 |
| gca ctg aac att ggt aac atg ctg tat aaa gat gat ttt gtg ggc<br>Ala Leu Asn Ile Gly Asn Met Leu Tyr Lys Asp Asp Phe Val Gly<br>1055                    1060                    1065 | 3204 |
| gcc ctg atc ttt tca ggc gct gtt atc ctg ctg gaa ttt atc ccg | 3249 |

|  |  |  |  |  |  |  |  |  |  |  |
|---|---|---|---|---|---|---|---|---|---|---|
| Ala | Leu | Ile | Phe | Ser | Gly | Ala | Val | Ile | Leu | Glu | Phe | Ile | Pro |
|  | 1070 |  |  |  | 1075 |  |  |  |  | 1080 |

```
gaa atc gcc att cca gta ctc ggt acc ttt gcg ctg gtg tcc tat       3294
Glu Ile Ala Ile Pro Val Leu Gly Thr Phe Ala Leu Val Ser Tyr
    1085                1090                1095 atc gca aac aaa gtt ttg act gtc cag acg atc gac aac gcg ctc       3339
Ile Ala Asn Lys Val Leu Thr Val Gln Thr Ile Asp Asn Ala Leu
1100                1105                1110 agt aaa cgt aac gaa aaa tgg gat gag gtg tat aag tat att gtt       3384
Ser Lys Arg Asn Glu Lys Trp Asp Glu Val Tyr Lys Tyr Ile Val
    1115                1120                1125 acc aac tgg ctc gct aaa gta aac acc cag att gac ctg att cgc       3429
Thr Asn Trp Leu Ala Lys Val Asn Thr Gln Ile Asp Leu Ile Arg
1130                1135                1140 aag aag atg aaa gaa gcg ctg gaa aac caa gca gaa gcg acc aaa       3474
Lys Lys Met Lys Glu Ala Leu Glu Asn Gln Ala Glu Ala Thr Lys
    1145                1150                1155 gct att atc aac tat caa tat aac cag tac aca gag gaa gaa aag       3519
Ala Ile Ile Asn Tyr Gln Tyr Asn Gln Tyr Thr Glu Glu Glu Lys
1160                1165                1170 aat aac atc aac ttc aac atc gac gac tta tct tca aag ctg aat       3564
Asn Asn Ile Asn Phe Asn Ile Asp Asp Leu Ser Ser Lys Leu Asn
    1175                1180                1185 gaa tct att aac aaa gcg atg att aat att aac aag ttc ttg aac       3609
Glu Ser Ile Asn Lys Ala Met Ile Asn Ile Asn Lys Phe Leu Asn
1190                1195                1200 caa tgt agt gtc agc tat ctg atg aac tcg atg atc cca tat ggt       3654
Gln Cys Ser Val Ser Tyr Leu Met Asn Ser Met Ile Pro Tyr Gly
    1205                1210                1215 gtg aaa cgt ctg gaa gac ttc gat gca agc ctt aaa gat gcc ctt       3699
Val Lys Arg Leu Glu Asp Phe Asp Ala Ser Leu Lys Asp Ala Leu
1220                1225                1230 ctg aag tat att tac gat aat cgc gga act ctt att ggc caa gtg       3744
Leu Lys Tyr Ile Tyr Asp Asn Arg Gly Thr Leu Ile Gly Gln Val
    1235                1240                1245 gat cgc tta aaa gat aaa gtc aac aac acg ctg agt aca gac atc       3789
Asp Arg Leu Lys Asp Lys Val Asn Asn Thr Leu Ser Thr Asp Ile
1250                1255                1260 cct ttt cag ctg tct aaa tat gtg gac aat cag cgc ctg ctg tcc       3834
Pro Phe Gln Leu Ser Lys Tyr Val Asp Asn Gln Arg Leu Leu Ser
    1265                1270                1275 acg ttt acg gaa tac atc aaa aac atc atc aac act agt att ctg       3879
Thr Phe Thr Glu Tyr Ile Lys Asn Ile Ile Asn Thr Ser Ile Leu
1280                1285                1290 aac ttg cgt tac gag agt aac cat ctg att gat ctg agc cgt tac       3924
Asn Leu Arg Tyr Glu Ser Asn His Leu Ile Asp Leu Ser Arg Tyr
    1295                1300                1305 gca tct aaa atc aac atc ggc tcg aag gtg aac ttc gat cct atc       3969
Ala Ser Lys Ile Asn Ile Gly Ser Lys Val Asn Phe Asp Pro Ile
1310                1315                1320 gac aaa aac cag att caa ttg ttc aac tta gaa tcg tca aag att       4014
Asp Lys Asn Gln Ile Gln Leu Phe Asn Leu Glu Ser Ser Lys Ile
    1325                1330                1335 gaa gtt atc tta aaa aat gcg att gta tat aat tca atg tac gaa       4059
Glu Val Ile Leu Lys Asn Ala Ile Val Tyr Asn Ser Met Tyr Glu
1340                1345                1350 aat ttc tct acg agc ttt tgg att cgt att ccg aaa tat ttc aac       4104
Asn Phe Ser Thr Ser Phe Trp Ile Arg Ile Pro Lys Tyr Phe Asn
    1355                1360                1365
```

```
agt atc tct tta aac aac gag tat act atc atc aat tgt atg gag      4149
Ser Ile Ser Leu Asn Asn Glu Tyr Thr Ile Ile Asn Cys Met Glu
    1370                1375                1380 aat aac agc ggg tgg aaa gtg agc ctt aac tat ggt gaa atc atc      4194
Asn Asn Ser Gly Trp Lys Val Ser Leu Asn Tyr Gly Glu Ile Ile
1385                1390                1395 tgg act ctg cag gac act caa gaa att aaa caa cgc gtg gtg ttt      4239
Trp Thr Leu Gln Asp Thr Gln Glu Ile Lys Gln Arg Val Val Phe
1400                1405                1410 aaa tac tca cag atg att aac atc tcg gat tat att aat cgc tgg      4284
Lys Tyr Ser Gln Met Ile Asn Ile Ser Asp Tyr Ile Asn Arg Trp
    1415                1420                1425 att ttt gtg aca att act aac aac cgg ctg aac aac agc aaa att      4329
Ile Phe Val Thr Ile Thr Asn Asn Arg Leu Asn Asn Ser Lys Ile
1430                1435                1440 tac att aac ggt cgc ctg atc gat cag aaa cca atc agt aat ctc      4374
Tyr Ile Asn Gly Arg Leu Ile Asp Gln Lys Pro Ile Ser Asn Leu
    1445                1450                1455 ggt aac att cac gca tcg aat aat atc atg ttc aaa ctg gat ggt      4419
Gly Asn Ile His Ala Ser Asn Asn Ile Met Phe Lys Leu Asp Gly
1460                1465                1470 tgt cgc gac acg cac cgt tac att tgg atc aaa tac ttc aat tta      4464
Cys Arg Asp Thr His Arg Tyr Ile Trp Ile Lys Tyr Phe Asn Leu
    1475                1480                1485 ttc gac aaa gaa ctc aac gaa aag gag att aag gat ctt tat gac      4509
Phe Asp Lys Glu Leu Asn Glu Lys Glu Ile Lys Asp Leu Tyr Asp
1490                1495                1500 aat cag tct aat tcg ggt att ctg aaa gac ttt tgg ggt gat tac      4554
Asn Gln Ser Asn Ser Gly Ile Leu Lys Asp Phe Trp Gly Asp Tyr
    1505                1510                1515 ctt cag tac gat aaa ccg tat tat atg tta aac tta tat gat ccg      4599
Leu Gln Tyr Asp Lys Pro Tyr Tyr Met Leu Asn Leu Tyr Asp Pro
1520                1525                1530 aat aaa tac gtt gac gtc aac aac gtt ggc att cgt ggc tat atg      4644
Asn Lys Tyr Val Asp Val Asn Asn Val Gly Ile Arg Gly Tyr Met
    1535                1540                1545 tat ctg aaa ggg ccg cgt ggc agc gtg atg acc act aac att tac      4689
Tyr Leu Lys Gly Pro Arg Gly Ser Val Met Thr Thr Asn Ile Tyr
1550                1555                1560 tta aac tcc tcc ctc tat cgc ggt act aaa ttt att atc aag aaa      4734
Leu Asn Ser Ser Leu Tyr Arg Gly Thr Lys Phe Ile Ile Lys Lys
    1565                1570                1575 tat gcc tct ggc aac aag gac aat atc gta cgc aat aac gat cgc      4779
Tyr Ala Ser Gly Asn Lys Asp Asn Ile Val Arg Asn Asn Asp Arg
1580                1585                1590 gtc tac att aac gtg gtg gtg aag aat aaa gaa tat cgt ctg gcg      4824
Val Tyr Ile Asn Val Val Val Lys Asn Lys Glu Tyr Arg Leu Ala
    1595                1600                1605 acc aat gct agt cag gcg ggc gtg gag aaa att ctg tct gca ctt      4869
Thr Asn Ala Ser Gln Ala Gly Val Glu Lys Ile Leu Ser Ala Leu
1610                1615                1620 gaa atc ccg gat gtg ggt aat tta tcc cag gtg gtt gtg atg aaa      4914
Glu Ile Pro Asp Val Gly Asn Leu Ser Gln Val Val Val Met Lys
    1625                1630                1635 agt aaa aat gac caa ggg atc acc aat aaa tgc aaa atg aat ctg      4959
Ser Lys Asn Asp Gln Gly Ile Thr Asn Lys Cys Lys Met Asn Leu
1640                1645                1650 caa gat aac aac ggc aac gac att ggt ttt atc ggc ttc cac caa      5004
Gln Asp Asn Asn Gly Asn Asp Ile Gly Phe Ile Gly Phe His Gln
    1655                1660                1665
```

```
ttc aat aat atc gcg aaa ctg gtg gcc tca aat tgg tac aac cgt   5049
Phe Asn Asn Ile Ala Lys Leu Val Ala Ser Asn Trp Tyr Asn Arg
    1670            1675                1680 cag att gag cgc agc tcc cgc act tta ggc tgt agc tgg gag ttc   5094
Gln Ile Glu Arg Ser Ser Arg Thr Leu Gly Cys Ser Trp Glu Phe
1685                1690                1695 att ccg gta gat gac ggt tgg gga gaa cgc cca ttg aaa gtc gac   5139
Ile Pro Val Asp Asp Gly Trp Gly Glu Arg Pro Leu Lys Val Asp
    1700            1705                1710 aag ctt ctg gta ccg cgc ggc agc aaa ctg cag ctc gag cac cac   5184
Lys Leu Leu Val Pro Arg Gly Ser Lys Leu Gln Leu Glu His His
    1715            1720                1725 cac cac cac cac tga                                           5199
His His His His
    1730
```

<210> SEQ ID NO 6
<211> LENGTH: 1732
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255
```

```
Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Asp Ile Met Pro Phe
                405                 410                 415

Val Asn Lys Gln Phe Asn Tyr Lys Asp Pro Val Asn Gly Val Asp Ile
            420                 425                 430

Ala Tyr Ile Lys Ile Pro Asn Ala Gly Gln Met Gln Pro Val Lys Ala
        435                 440                 445

Phe Lys Ile His Asn Lys Ile Trp Val Ile Pro Glu Arg Asp Thr Phe
450                 455                 460

Thr Asn Pro Glu Glu Gly Asp Leu Asn Pro Pro Glu Ala Lys Gln
465                 470                 475                 480

Val Pro Val Ser Tyr Tyr Asp Ser Thr Tyr Leu Ser Thr Asp Asn Glu
            485                 490                 495

Lys Asp Asn Tyr Leu Lys Gly Val Thr Lys Leu Phe Glu Arg Ile Tyr
        500                 505                 510

Ser Thr Asp Leu Gly Arg Met Leu Leu Thr Ser Ile Val Arg Gly Ile
    515                 520                 525

Pro Phe Trp Gly Gly Ser Thr Ile Asp Thr Glu Leu Lys Val Ile Asp
530                 535                 540

Thr Asn Cys Ile Asn Val Ile Gln Pro Asp Gly Ser Tyr Arg Ser Glu
545                 550                 555                 560

Glu Leu Asn Leu Val Ile Ile Gly Pro Ser Ala Asp Ile Ile Gln Phe
                565                 570                 575

Glu Cys Lys Ser Phe Gly His Glu Val Leu Asn Leu Thr Arg Asn Gly
            580                 585                 590

Tyr Gly Ser Thr Gln Tyr Ile Arg Phe Ser Pro Asp Phe Thr Phe Gly
        595                 600                 605

Phe Glu Glu Ser Leu Glu Val Asp Thr Asn Pro Leu Leu Gly Ala Gly
    610                 615                 620

Lys Phe Ala Thr Asp Pro Ala Val Thr Leu Ala His Glu Leu Ile His
625                 630                 635                 640

Ala Gly His Arg Leu Tyr Gly Ile Ala Ile Asn Pro Asn Arg Val Phe
                645                 650                 655

Lys Val Asn Thr Asn Ala Tyr Tyr Glu Met Ser Gly Leu Glu Val Ser
            660                 665                 670
```

-continued

Phe Glu Glu Leu Arg Thr Phe Gly His Asp Ala Lys Phe Ile Asp
        675                 680                 685

Ser Leu Gln Glu Asn Gln Phe Arg Leu Tyr Tyr Asn Lys Phe Lys
        690                 695                 700

Asp Ile Ala Ser Thr Leu Asn Lys Ala Lys Ser Ile Val Gly Thr Thr
705                 710                 715                 720

Ala Ser Leu Gln Tyr Met Lys Asn Val Phe Lys Glu Lys Tyr Leu Leu
            725                 730                 735

Ser Glu Asp Thr Ser Gly Lys Phe Ser Val Asp Lys Leu Lys Phe Asp
            740                 745                 750

Lys Leu Tyr Lys Met Leu Thr Glu Ile Tyr Thr Glu Asp Asn Phe Val
        755                 760                 765

Lys Phe Phe Lys Val Leu Asn Arg Lys Thr Tyr Leu Asn Phe Asp Lys
        770                 775                 780

Ala Val Phe Lys Ile Asn Ile Val Pro Lys Val Asn Tyr Thr Ile Tyr
785                 790                 795                 800

Asp Gly Phe Asn Leu Arg Asn Thr Asn Leu Ala Ala Asn Phe Asn Gly
            805                 810                 815

Gln Asn Thr Glu Ile Asn Asn Met Asn Phe Thr Lys Leu Lys Asn Phe
            820                 825                 830

Thr Gly Leu Phe Glu Phe Tyr Lys Leu Leu Cys Val Arg Gly Ile Ile
        835                 840                 845

Thr Ser Lys Thr Lys Ser Leu Val Pro Arg Gly Ser Asn Lys Ala Leu
        850                 855                 860

Asn Asp Leu Cys Ile Lys Val Asn Asn Trp Asp Leu Phe Phe Ser Pro
865                 870                 875                 880

Ser Glu Asp Asn Phe Thr Asn Asp Leu Asn Lys Gly Glu Glu Ile Thr
            885                 890                 895

Ser Asp Thr Asn Ile Glu Ala Ala Glu Glu Asn Ile Ser Leu Asp Leu
            900                 905                 910

Ile Gln Gln Tyr Tyr Leu Thr Phe Asn Phe Asp Asn Glu Pro Glu Asn
        915                 920                 925

Ile Ser Ile Glu Asn Leu Ser Ser Asp Ile Ile Gly Gln Leu Glu Leu
        930                 935                 940

Met Pro Asn Ile Glu Arg Phe Pro Asn Gly Lys Lys Tyr Glu Leu Asp
945                 950                 955                 960

Lys Tyr Thr Met Phe His Tyr Leu Arg Ala Gln Glu Phe Glu His Gly
            965                 970                 975

Lys Ser Arg Ile Ala Leu Thr Asn Ser Val Asn Glu Ala Leu Leu Asn
            980                 985                 990

Pro Ser Arg Val Tyr Thr Phe Phe Ser Ser Asp Tyr Val Lys Lys Val
        995                 1000                1005

Asn Lys Ala Thr Glu Ala Ala Met Phe Leu Gly Trp Val Glu Gln
    1010                1015                1020

Leu Val Tyr Asp Phe Thr Asp Glu Thr Ser Glu Val Ser Thr Thr
    1025                1030                1035

Asp Lys Ile Ala Asp Ile Thr Ile Ile Ile Pro Tyr Ile Gly Pro
    1040                1045                1050

Ala Leu Asn Ile Gly Asn Met Leu Tyr Lys Asp Asp Phe Val Gly
    1055                1060                1065

Ala Leu Ile Phe Ser Gly Ala Val Ile Leu Leu Glu Phe Ile Pro
    1070                1075                1080

Glu Ile Ala Ile Pro Val Leu Gly Thr Phe Ala Leu Val Ser Tyr

-continued

```
            1085                1090                1095
Ile Ala Asn Lys Val Leu Thr Val Gln Thr Ile Asp Asn Ala Leu
        1100                1105                1110
Ser Lys Arg Asn Glu Lys Trp Asp Glu Val Tyr Lys Tyr Ile Val
        1115                1120                1125
Thr Asn Trp Leu Ala Lys Val Asn Thr Gln Ile Asp Leu Ile Arg
        1130                1135                1140
Lys Lys Met Lys Glu Ala Leu Glu Asn Gln Ala Glu Ala Thr Lys
        1145                1150                1155
Ala Ile Ile Asn Tyr Gln Tyr Asn Gln Tyr Thr Glu Glu Glu Lys
        1160                1165                1170
Asn Asn Ile Asn Phe Asn Ile Asp Asp Leu Ser Ser Lys Leu Asn
        1175                1180                1185
Glu Ser Ile Asn Lys Ala Met Ile Asn Ile Asn Lys Phe Leu Asn
        1190                1195                1200
Gln Cys Ser Val Ser Tyr Leu Met Asn Ser Met Ile Pro Tyr Gly
        1205                1210                1215
Val Lys Arg Leu Glu Asp Phe Asp Ala Ser Leu Lys Asp Ala Leu
        1220                1225                1230
Leu Lys Tyr Ile Tyr Asp Asn Arg Gly Thr Leu Ile Gly Gln Val
        1235                1240                1245
Asp Arg Leu Lys Asp Lys Val Asn Asn Thr Leu Ser Thr Asp Ile
        1250                1255                1260
Pro Phe Gln Leu Ser Lys Tyr Val Asp Asn Gln Arg Leu Leu Ser
        1265                1270                1275
Thr Phe Thr Glu Tyr Ile Lys Asn Ile Ile Asn Thr Ser Ile Leu
        1280                1285                1290
Asn Leu Arg Tyr Glu Ser Asn His Leu Ile Asp Leu Ser Arg Tyr
        1295                1300                1305
Ala Ser Lys Ile Asn Ile Gly Ser Lys Val Asn Phe Asp Pro Ile
        1310                1315                1320
Asp Lys Asn Gln Ile Gln Leu Phe Asn Leu Glu Ser Ser Lys Ile
        1325                1330                1335
Glu Val Ile Leu Lys Asn Ala Ile Val Tyr Asn Ser Met Tyr Glu
        1340                1345                1350
Asn Phe Ser Thr Ser Phe Trp Ile Arg Ile Pro Lys Tyr Phe Asn
        1355                1360                1365
Ser Ile Ser Leu Asn Asn Glu Tyr Thr Ile Ile Asn Cys Met Glu
        1370                1375                1380
Asn Asn Ser Gly Trp Lys Val Ser Leu Asn Tyr Gly Glu Ile Ile
        1385                1390                1395
Trp Thr Leu Gln Asp Thr Gln Glu Ile Lys Gln Arg Val Val Phe
        1400                1405                1410
Lys Tyr Ser Gln Met Ile Asn Ile Ser Asp Tyr Ile Asn Arg Trp
        1415                1420                1425
Ile Phe Val Thr Ile Thr Asn Asn Arg Leu Asn Asn Ser Lys Ile
        1430                1435                1440
Tyr Ile Asn Gly Arg Leu Ile Asp Gln Lys Pro Ile Ser Asn Leu
        1445                1450                1455
Gly Asn Ile His Ala Ser Asn Asn Ile Met Phe Lys Leu Asp Gly
        1460                1465                1470
Cys Arg Asp Thr His Arg Tyr Ile Trp Ile Lys Tyr Phe Asn Leu
        1475                1480                1485
```

```
Phe Asp Lys Glu Leu Asn Glu Lys Ile Lys Asp Leu Tyr Asp
    1490            1495                1500

Asn Gln Ser Asn Ser Gly Ile Leu Lys Asp Phe Trp Gly Asp Tyr
    1505            1510                1515

Leu Gln Tyr Asp Lys Pro Tyr Tyr Met Leu Asn Leu Tyr Asp Pro
    1520            1525                1530

Asn Lys Tyr Val Asp Val Asn Asn Val Gly Ile Arg Gly Tyr Met
    1535            1540                1545

Tyr Leu Lys Gly Pro Arg Gly Ser Val Met Thr Thr Asn Ile Tyr
    1550            1555                1560

Leu Asn Ser Ser Leu Tyr Arg Gly Thr Lys Phe Ile Ile Lys Lys
    1565            1570                1575

Tyr Ala Ser Gly Asn Lys Asp Asn Ile Val Arg Asn Asn Asp Arg
    1580            1585                1590

Val Tyr Ile Asn Val Val Val Lys Asn Lys Glu Tyr Arg Leu Ala
    1595            1600                1605

Thr Asn Ala Ser Gln Ala Gly Val Glu Lys Ile Leu Ser Ala Leu
    1610            1615                1620

Glu Ile Pro Asp Val Gly Asn Leu Ser Gln Val Val Val Met Lys
    1625            1630                1635

Ser Lys Asn Asp Gln Gly Ile Thr Asn Lys Cys Lys Met Asn Leu
    1640            1645                1650

Gln Asp Asn Asn Gly Asn Asp Ile Gly Phe Ile Gly Phe His Gln
    1655            1660                1665

Phe Asn Asn Ile Ala Lys Leu Val Ala Ser Asn Trp Tyr Asn Arg
    1670            1675                1680

Gln Ile Glu Arg Ser Ser Arg Thr Leu Gly Cys Ser Trp Glu Phe
    1685            1690                1695

Ile Pro Val Asp Asp Gly Trp Gly Glu Arg Pro Leu Lys Val Asp
    1700            1705                1710

Lys Leu Leu Val Pro Arg Gly Ser Lys Leu Gln Leu Glu His His
    1715            1720                1725

His His His His
    1730

<210> SEQ ID NO 7
<211> LENGTH: 1296
<212> TYPE: PRT
<213> ORGANISM: Clostridium botulinum

<400> SEQUENCE: 7

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
```

```
                100                 105                 110
Arg Gly Ile Pro Phe Trp Gly Gly Ser Thr Ile Asp Thr Glu Leu Lys
            115                 120                 125
Val Ile Asp Thr Asn Cys Ile Asn Val Ile Gln Pro Asp Gly Ser Tyr
            130                 135             140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
            195                 200                 205
Gly Ala Gly Lys Phe Ala Thr Asp Pro Ala Val Thr Leu Ala His Glu
            210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
            275                 280                 285
Lys Phe Lys Asp Ile Ala Ser Thr Leu Asn Lys Ala Lys Ser Ile Val
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
```

```
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
        595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
        675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
                725                 730                 735
Glu Asn Gln Ala Glu Ala Thr Lys Ala Ile Ile Asn Tyr Gln Tyr Asn
            740                 745                 750
Gln Tyr Thr Glu Glu Glu Lys Asn Asn Ile Asn Phe Asn Ile Asp Asp
        755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
                805                 810                 815
Asp Ala Leu Leu Lys Tyr Ile Tyr Asp Asn Arg Gly Thr Leu Ile Gly
            820                 825                 830
Gln Val Asp Arg Leu Lys Asp Lys Val Asn Asn Thr Leu Ser Thr Asp
        835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
            900                 905                 910
Gln Ile Gln Leu Phe Asn Leu Glu Ser Ser Lys Ile Glu Val Ile Leu
        915                 920                 925
Lys Asn Ala Ile Val Tyr Asn Ser Met Tyr Glu Asn Phe Ser Thr Ser
930                 935                 940
```

```
Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 8
<211> LENGTH: 1291
<212> TYPE: PRT
<213> ORGANISM: Clostridium botulinum

<400> SEQUENCE: 8
```

-continued

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
            85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
            405                 410                 415
```

```
Asn Lys Gln Ala Tyr Glu Glu Ile Ser Lys Glu His Leu Ala Val Tyr
                420                 425                 430
Lys Ile Gln Met Cys Lys Ser Val Lys Ala Pro Gly Ile Cys Ile Asp
                435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
                500                 505                 510
Asp Phe Asn Val Asp Val Pro Val Tyr Glu Lys Gln Pro Ala Ile Lys
                515                 520                 525
Lys Ile Phe Thr Asp Glu Asn Thr Ile Phe Gln Tyr Leu Tyr Ser Gln
                530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Ser Met Asp
                565                 570                 575
Tyr Ile Lys Thr Ala Asn Lys Val Val Glu Ala Gly Leu Phe Ala Gly
                580                 585                 590
Trp Val Lys Gln Ile Val Asn Asp Phe Val Ile Glu Ala Asn Lys Ser
                595                 600                 605
Asn Thr Met Asp Lys Ile Ala Asp Ile Ser Leu Ile Val Pro Tyr Ile
610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
                660                 665                 670
Asp Asn Lys Asn Lys Ile Ile Lys Thr Ile Asp Asn Ala Leu Thr Lys
                675                 680                 685
Arg Asn Glu Lys Trp Ser Asp Met Tyr Gly Leu Ile Val Ala Gln Trp
690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Arg Tyr Asn Ile Tyr Ser Glu Lys Glu Lys Ser Asn Ile Asn Ile Asp
                740                 745                 750
Phe Asn Asp Ile Asn Ser Lys Leu Asn Glu Gly Ile Asn Gln Ala Ile
                755                 760                 765
Asp Asn Ile Asn Asn Phe Ile Asn Gly Cys Ser Val Ser Tyr Leu Met
770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
Leu Ile Gly Ser Ala Glu Tyr Glu Lys Ser Lys Val Asn Lys Tyr Leu
                820                 825                 830
Lys Thr Ile Met Pro Phe Asp Leu Ser Ile Tyr Thr Asn Asp Thr Ile
```

```
                835                840                845
Leu Ile Glu Met Phe Asn Lys Tyr Asn Ser Glu Ile Leu Asn Asn Ile
    850                855                860
Ile Leu Asn Leu Arg Tyr Lys Asp Asn Leu Ile Asp Leu Ser Gly
865                870                875                880
Tyr Gly Ala Lys Val Glu Val Tyr Asp Gly Val Glu Leu Asn Asp Lys
                885                890                895
Asn Gln Phe Lys Leu Thr Ser Ser Ala Asn Ser Lys Ile Arg Val Thr
            900                905                910
Gln Asn Gln Asn Ile Ile Phe Asn Ser Val Phe Leu Asp Phe Ser Val
                915                920                925
Ser Phe Trp Ile Arg Ile Pro Lys Tyr Lys Asn Asp Gly Ile Gln Asn
    930                935                940
Tyr Ile His Asn Glu Tyr Thr Ile Ile Asn Cys Met Lys Asn Asn Ser
945                950                955                960
Gly Trp Lys Ile Ser Ile Arg Gly Asn Arg Ile Ile Trp Thr Leu Ile
                965                970                975
Asp Ile Asn Gly Lys Thr Lys Ser Val Phe Phe Glu Tyr Asn Ile Arg
            980                985                990
Glu Asp Ile Ser Glu Tyr Ile Asn  Arg Trp Phe Phe Val  Thr Ile Thr
            995                1000                1005
Asn Asn  Leu Asn Asn Ala Lys  Ile Tyr Ile Asn Gly  Lys Leu Glu
    1010                1015                1020
Ser Asn  Thr Asp Ile Lys Asp  Ile Arg Glu Val Ile  Ala Asn Gly
    1025                1030                1035
Glu Ile  Ile Phe Lys Leu Asp  Gly Asp Ile Asp Arg  Thr Gln Phe
    1040                1045                1050
Ile Trp  Met Lys Tyr Phe Ser  Ile Phe Asn Thr Glu  Leu Ser Gln
    1055                1060                1065
Ser Asn  Ile Glu Glu Arg Tyr  Lys Ile Gln Ser Tyr  Ser Glu Tyr
    1070                1075                1080
Leu Lys  Asp Phe Trp Gly Asn  Pro Leu Met Tyr Asn  Lys Glu Tyr
    1085                1090                1095
Tyr Met  Phe Asn Ala Gly Asn  Lys Asn Ser Tyr Ile  Lys Leu Lys
    1100                1105                1110
Lys Asp  Ser Pro Val Gly Glu  Ile Leu Thr Arg Ser  Lys Tyr Asn
    1115                1120                1125
Gln Asn  Ser Lys Tyr Ile Asn  Tyr Arg Asp Leu Tyr  Ile Gly Glu
    1130                1135                1140
Lys Phe  Ile Ile Arg Arg Lys  Ser Asn Ser Gln Ser  Ile Asn Asp
    1145                1150                1155
Asp Ile  Val Arg Lys Glu Asp  Tyr Ile Tyr Leu Asp  Phe Phe Asn
    1160                1165                1170
Leu Asn  Gln Glu Trp Arg Val  Tyr Thr Tyr Lys Tyr  Phe Lys Lys
    1175                1180                1185
Glu Glu  Glu Lys Leu Phe Leu  Ala Pro Ile Ser Asp  Ser Asp Glu
    1190                1195                1200
Phe Tyr  Asn Thr Ile Gln Ile  Lys Glu Tyr Asp Glu  Gln Pro Thr
    1205                1210                1215
Tyr Ser  Cys Gln Leu Leu Phe  Lys Lys Asp Glu Glu  Ser Thr Asp
    1220                1225                1230
Glu Ile  Gly Leu Ile Gly Ile  His Arg Phe Tyr Glu  Ser Gly Ile
    1235                1240                1245
```

Val Phe Glu Glu Tyr Lys Asp Tyr Phe Cys Ile Ser Lys Trp Tyr
1250                1255                1260

Leu Lys Glu Val Lys Arg Lys Pro Tyr Asn Leu Lys Leu Gly Cys
1265                1270                1275

Asn Trp Gln Phe Ile Pro Lys Asp Glu Gly Trp Thr Glu
1280                1285                1290

<210> SEQ ID NO 9
<211> LENGTH: 1291
<212> TYPE: PRT
<213> ORGANISM: Clostridium botulinum

<400> SEQUENCE: 9

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser

```
            325                 330                 335
Ser Gly Glu Val Thr Val Asn Arg Asn Lys Phe Val Glu Leu Tyr Asn
            340                 345                 350
Glu Leu Thr Gln Ile Phe Thr Glu Phe Asn Tyr Ala Lys Ile Tyr Asn
            355                 360                 365
Val Gln Asn Arg Lys Ile Tyr Leu Ser Asn Val Tyr Thr Pro Val Thr
            370                 375                 380
Ala Asn Ile Leu Asp Asp Asn Val Tyr Asp Ile Gln Asn Gly Phe Asn
385                 390                 395                 400
Ile Pro Lys Ser Asn Leu Asn Val Leu Phe Met Gly Gln Asn Leu Ser
            405                 410                 415
Arg Asn Pro Ala Leu Arg Lys Val Asn Pro Glu Asn Met Leu Tyr Leu
            420                 425                 430
Phe Thr Lys Phe Cys His Lys Ala Ile Asp Gly Arg Ser Leu Tyr Asn
            435                 440                 445
Lys Thr Leu Asp Cys Arg Glu Leu Leu Val Lys Asn Thr Asp Leu Pro
            450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
            485                 490                 495
Val Asp Gln Val Ile Leu Ser Lys Asn Thr Ser Glu His Gly Gln Leu
            500                 505                 510
Asp Leu Leu Tyr Pro Ser Ile Asp Ser Glu Ser Glu Ile Leu Pro Gly
            515                 520                 525
Glu Asn Gln Val Phe Tyr Asp Asn Arg Thr Gln Asn Val Asp Tyr Leu
            530                 535                 540
Asn Ser Tyr Tyr Tyr Leu Glu Ser Gln Lys Leu Ser Asp Asn Val Glu
545                 550                 555                 560
Asp Phe Thr Phe Thr Arg Ser Ile Glu Glu Ala Leu Asp Asn Ser Ala
            565                 570                 575
Lys Val Tyr Thr Tyr Phe Pro Thr Leu Ala Asn Lys Val Asn Ala Gly
            580                 585                 590
Val Gln Gly Gly Leu Phe Leu Met Trp Ala Asn Asp Val Val Glu Asp
            595                 600                 605
Phe Thr Thr Asn Ile Leu Arg Lys Asp Thr Leu Asp Lys Ile Ser Asp
            610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
            645                 650                 655
Thr Ile Leu Leu Glu Ala Phe Pro Glu Phe Thr Ile Pro Ala Leu Gly
            660                 665                 670
Ala Phe Val Ile Tyr Ser Lys Val Gln Glu Arg Asn Glu Ile Ile Lys
            675                 680                 685
Thr Ile Asp Asn Cys Leu Glu Gln Arg Ile Lys Arg Trp Lys Asp Ser
            690                 695                 700
Tyr Glu Trp Met Met Gly Thr Trp Leu Ser Arg Ile Ile Thr Gln Phe
705                 710                 715                 720
Asn Asn Ile Ser Tyr Gln Met Tyr Asp Ser Leu Asn Tyr Gln Ala Gly
            725                 730                 735
Ala Ile Lys Ala Lys Ile Asp Leu Glu Tyr Lys Lys Tyr Ser Gly Ser
            740                 745                 750
```

-continued

```
Asp Lys Glu Asn Ile Lys Ser Gln Val Glu Asn Leu Lys Asn Ser Leu
            755                 760                 765
Asp Val Lys Ile Ser Glu Ala Met Asn Asn Ile Asn Lys Phe Ile Arg
770                 775                 780
Glu Cys Ser Val Thr Tyr Leu Phe Lys Asn Met Leu Pro Lys Val Ile
785                 790                 795                 800
Asp Glu Leu Asn Glu Phe Asp Arg Asn Thr Lys Ala Lys Leu Ile Asn
                805                 810                 815
Leu Ile Asp Ser His Asn Ile Ile Leu Val Gly Glu Val Asp Lys Leu
            820                 825                 830
Lys Ala Lys Val Asn Asn Ser Phe Gln Asn Thr Ile Pro Phe Asn Ile
        835                 840                 845
Phe Ser Tyr Thr Asn Asn Ser Leu Leu Lys Asp Ile Ile Asn Glu Tyr
    850                 855                 860
Phe Asn Asn Ile Asn Asp Ser Lys Ile Leu Ser Leu Gln Asn Arg Lys
865                 870                 875                 880
Asn Thr Leu Val Asp Thr Ser Gly Tyr Asn Ala Glu Val Ser Glu Glu
                885                 890                 895
Gly Asp Val Gln Leu Asn Pro Ile Phe Pro Phe Asp Phe Lys Leu Gly
            900                 905                 910
Ser Ser Gly Glu Asp Arg Gly Lys Val Ile Val Thr Gln Asn Glu Asn
        915                 920                 925
Ile Val Tyr Asn Ser Met Tyr Glu Ser Phe Ser Ile Ser Phe Trp Ile
    930                 935                 940
Arg Ile Asn Lys Trp Val Ser Asn Leu Pro Gly Tyr Thr Ile Ile Asp
945                 950                 955                 960
Ser Val Lys Asn Asn Ser Gly Trp Ser Ile Gly Ile Ile Ser Asn Phe
                965                 970                 975
Leu Val Phe Thr Leu Lys Gln Asn Glu Asp Ser Glu Gln Ser Ile Asn
            980                 985                 990
Phe Ser Tyr Asp Ile Ser Asn Asn  Ala Pro Gly Tyr Asn  Lys Trp Phe
        995                 1000                 1005
Phe Val  Thr Val Thr Asn Asn  Met Met Gly Asn Met  Lys Ile Tyr
    1010                 1015                 1020
Ile Asn  Gly Lys Leu Ile Asp  Thr Ile Lys Val Lys  Glu Leu Thr
    1025                 1030                 1035
Gly Ile  Asn Phe Ser Lys Thr  Ile Thr Phe Glu Ile  Asn Lys Ile
    1040                 1045                 1050
Pro Asp  Thr Gly Leu Ile Thr  Ser Asp Ser Asp Asn  Ile Asn Met
    1055                 1060                 1065
Trp Ile  Arg Asp Phe Tyr Ile  Phe Ala Lys Glu Leu  Asp Gly Lys
    1070                 1075                 1080
Asp Ile  Asn Ile Leu Phe Asn  Ser Leu Gln Tyr Thr  Asn Val Val
    1085                 1090                 1095
Lys Asp  Tyr Trp Gly Asn Asp  Leu Arg Tyr Asn Lys  Glu Tyr Tyr
    1100                 1105                 1110
Met Val  Asn Ile Asp Tyr Leu  Asn Arg Tyr Met Tyr  Ala Asn Ser
    1115                 1120                 1125
Arg Gln  Ile Val Phe Asn Thr  Arg Arg Asn Asn Asn  Asp Phe Asn
    1130                 1135                 1140
Glu Gly  Tyr Lys Ile Ile Ile  Lys Arg Ile Arg Gly  Asn Thr Asn
    1145                 1150                 1155
```

```
Asp Thr Arg Val Arg Gly Gly Asp Ile Leu Tyr Phe Asp Met Thr
    1160                1165                1170

Ile Asn Asn Lys Ala Tyr Asn Leu Phe Met Lys Asn Glu Thr Met
    1175                1180                1185

Tyr Ala Asp Asn His Ser Thr Glu Asp Ile Tyr Ala Ile Gly Leu
    1190                1195                1200

Arg Glu Gln Thr Lys Asp Ile Asn Asp Asn Ile Ile Phe Gln Ile
    1205                1210                1215

Gln Pro Met Asn Asn Thr Tyr Tyr Tyr Ala Ser Gln Ile Phe Lys
    1220                1225                1230

Ser Asn Phe Asn Gly Glu Asn Ile Ser Gly Ile Cys Ser Ile Gly
    1235                1240                1245

Thr Tyr Arg Phe Arg Leu Gly Gly Asp Trp Tyr Arg His Asn Tyr
    1250                1255                1260

Leu Val Pro Thr Val Lys Gln Gly Asn Tyr Ala Ser Leu Leu Glu
    1265                1270                1275

Ser Thr Ser Thr His Trp Gly Phe Val Pro Val Ser Glu
    1280                1285                1290

<210> SEQ ID NO 10
<211> LENGTH: 1276
<212> TYPE: PRT
<213> ORGANISM: Clostridium botulinum

<400> SEQUENCE: 10

Met Thr Trp Pro Val Lys Asp Phe Asn Tyr Ser Asp Pro Val Asn
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
                35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
                115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
                180                 185                 190

Lys Val Ala Pro Glu Phe Leu Leu Thr Phe Ser Asp Val Thr Ser Asn
                195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240
```

-continued

Ile Asn Ile Pro Ser Asp Lys Arg Ile Arg Pro Gln Val Ser Glu Gly
            245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
            290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Arg His Tyr Leu Pro Val Phe
            370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
            405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
            435                 440                 445

Thr Cys Ile Lys Val Lys Asn Asn Arg Leu Pro Tyr Val Ala Asp Lys
450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
            485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
            515                 520                 525

Phe Tyr Asp Asp Ile Thr Lys Tyr Val Asp Tyr Leu Asn Ser Tyr Tyr
            530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
            565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
            595                 600                 605

Ile Met Lys Lys Asp Thr Leu Asp Lys Ile Ser Asp Val Ser Val Ile
610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
            645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
            675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
            725                 730                 735

Lys Ile Asp Leu Glu Tyr Lys Lys Tyr Ser Gly Ser Asp Lys Glu Asn
            740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
            805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
            835                 840                 845

Asn Asn Ser Leu Leu Lys Asp Ile Ile Asn Glu Tyr Phe Asn Ser Ile
    850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
            885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
            915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
            965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
            995                 1000                1005

Asn Asn Ile Met Gly Tyr Met Lys Leu Tyr Ile Asn Gly Glu Leu
            1010                1015                1020

Lys Gln Ser Gln Lys Ile Glu Asp Leu Asp Glu Val Lys Leu Asp
            1025                1030                1035

Lys Thr Ile Val Phe Gly Ile Asp Glu Asn Ile Asp Glu Asn Gln
            1040                1045                1050

Met Leu Trp Ile Arg Asp Phe Asn Ile Phe Ser Lys Glu Leu Ser
            1055                1060                1065

Asn Glu Asp Ile Asn Ile Val Tyr Glu Gly Gln Ile Leu Arg Asn

-continued

```
                1070                1075                1080

Val Ile Lys Asp Tyr Trp Gly Asn Pro Leu Lys Phe Asp Thr Glu
            1085                1090                1095

Tyr Tyr Ile Ile Asn Asp Asn Tyr Ile Asp Arg Tyr Ile Ala Pro
        1100                1105                1110

Glu Ser Asn Val Leu Val Leu Val Gln Tyr Pro Asp Arg Ser Lys
    1115                1120                1125

Leu Tyr Thr Gly Asn Pro Ile Thr Ile Lys Ser Val Ser Asp Lys
1130                1135                1140

Asn Pro Tyr Ser Arg Ile Leu Asn Gly Asp Asn Ile Ile Leu His
    1145                1150                1155

Met Leu Tyr Asn Ser Arg Lys Tyr Met Ile Ile Arg Asp Thr Asp
        1160                1165                1170

Thr Ile Tyr Ala Thr Gln Gly Gly Glu Cys Ser Gln Asn Cys Val
            1175                1180                1185

Tyr Ala Leu Lys Leu Gln Ser Asn Leu Gly Asn Tyr Gly Ile Gly
                1190                1195                1200

Ile Phe Ser Ile Lys Asn Ile Val Ser Lys Asn Lys Tyr Cys Ser
                    1205                1210                1215

Gln Ile Phe Ser Ser Phe Arg Glu Asn Thr Met Leu Leu Ala Asp
1220                1225                1230

Ile Tyr Lys Pro Trp Arg Phe Ser Phe Lys Asn Ala Tyr Thr Pro
    1235                1240                1245

Val Ala Val Thr Asn Tyr Glu Thr Lys Leu Leu Ser Thr Ser Ser
        1250                1255                1260

Phe Trp Lys Phe Ile Ser Arg Asp Pro Gly Trp Val Glu
            1265                1270                1275

<210> SEQ ID NO 11
<211> LENGTH: 1252
<212> TYPE: PRT
<213> ORGANISM: Clostridium botulinum

<400> SEQUENCE: 11

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160
```

```
Asn Ser Ser Asn Ile Ser Leu Arg Asn Asn Tyr Met Pro Ser Asn His
            165                 170                 175
Gly Phe Gly Ser Ile Ala Ile Val Thr Phe Ser Pro Glu Tyr Ser Phe
        180                 185                 190
Arg Phe Asn Asp Asn Ser Met Asn Glu Phe Ile Gln Asp Pro Ala Leu
        195                 200                 205
Thr Leu Met His Glu Leu Ile His Ser Leu His Gly Leu Tyr Gly Ala
        210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
        275                 280                 285
Val Gln Val Ser Asn Pro Leu Leu Asn Pro Tyr Lys Asp Val Phe Glu
        290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
        370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
        435                 440                 445
Asn Thr Pro Lys Glu Ile Asp Asp Thr Val Thr Ser Asn Asn Asn Tyr
        450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
        515                 520                 525
Pro Glu Gly Glu Asn Asn Val Asn Leu Thr Ser Ser Ile Asp Thr Ala
        530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
```

```
                580                 585                 590
Val Asp Lys Ile Ala Asp Ile Ser Ile Val Pro Tyr Ile Gly Leu
            595                 600                 605

Ala Leu Asn Ile Gly Asn Glu Ala Gln Lys Gly Asn Phe Lys Asp Ala
    610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Leu Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005
```

```
Gly Asn Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Phe Ile
    1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
    1115                1120                1125

Ile Gln Arg Val Asn Asn Ser Ser Thr Asn Asp Asn Leu Val Arg
    1130                1135                1140

Lys Asn Asp Gln Val Tyr Ile Asn Phe Val Ala Ser Lys Thr His
    1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
    1175                1180                1185

Val Met Asn Ser Val Gly Asn Asn Cys Thr Met Asn Phe Lys Asn
    1190                1195                1200

Asn Asn Gly Asn Asn Ile Gly Leu Leu Gly Phe Lys Ala Asp Thr
    1205                1210                1215

Val Val Ala Ser Thr Trp Tyr Tyr Thr His Met Arg Asp His Thr
    1220                1225                1230

Asn Ser Asn Gly Cys Phe Trp Asn Phe Ile Ser Glu Glu His Gly
    1235                1240                1245

Trp Gln Glu Lys
    1250

<210> SEQ ID NO 12
<211> LENGTH: 1274
<212> TYPE: PRT
<213> ORGANISM: Clostridium botulinum

<400> SEQUENCE: 12

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
        50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
```

```
                100                 105                 110
Tyr Ala Lys Pro Tyr Leu Gly Asn Asp His Thr Pro Ile Asp Glu Phe
            115                 120                 125
Ser Pro Val Thr Arg Thr Thr Ser Val Asn Ile Lys Leu Ser Thr Asn
            130                 135                 140
Val Glu Ser Ser Met Leu Leu Asn Leu Leu Val Leu Gly Ala Gly Pro
145                 150                 155                 160
Asp Ile Phe Glu Ser Cys Cys Tyr Pro Val Arg Lys Leu Ile Asp Pro
            165                 170                 175
Asp Val Val Tyr Asp Pro Ser Asn Tyr Gly Phe Gly Ser Ile Asn Ile
            180                 185                 190
Val Thr Phe Ser Pro Glu Tyr Glu Tyr Thr Phe Asn Asp Ile Ser Gly
            195                 200                 205
Gly His Asn Ser Ser Thr Glu Ser Phe Ile Ala Asp Pro Ala Ile Ser
            210                 215                 220
Leu Ala His Glu Leu Ile His Ala Leu His Gly Leu Tyr Gly Ala Arg
225                 230                 235                 240
Gly Val Thr Tyr Glu Glu Thr Ile Glu Val Lys Gln Ala Pro Leu Met
            245                 250                 255
Ile Ala Glu Lys Pro Ile Arg Leu Glu Glu Phe Leu Thr Phe Gly Gly
            260                 265                 270
Gln Asp Leu Asn Ile Ile Thr Ser Ala Met Lys Glu Lys Ile Tyr Asn
            275                 280                 285
Asn Leu Leu Ala Asn Tyr Glu Lys Ile Ala Thr Arg Leu Ser Glu Val
290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
            325                 330                 335
Asn Glu Asn Lys Phe Asn Glu Ile Tyr Lys Lys Leu Tyr Ser Phe Thr
            340                 345                 350
Glu Ser Asp Leu Ala Asn Lys Phe Lys Val Lys Cys Arg Asn Thr Tyr
            355                 360                 365
Phe Ile Lys Tyr Glu Phe Leu Lys Val Pro Asn Leu Leu Asp Asp Asp
            370                 375                 380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
            405                 410                 415
Pro Asp Lys Gly Leu Val Glu Lys Ile Val Lys Phe Cys Lys Ser Val
            420                 425                 430
Ile Pro Arg Lys Gly Thr Lys Ala Pro Pro Arg Leu Cys Ile Arg Val
            435                 440                 445
Asn Asn Ser Glu Leu Phe Phe Val Ala Ser Glu Ser Ser Tyr Asn Glu
            450                 455                 460
Asn Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
            485                 490                 495
Gln Thr Ile Pro Gln Ile Ser Asn Arg Thr Leu Asn Thr Leu Val Gln
            500                 505                 510
Asp Asn Ser Tyr Val Pro Arg Tyr Asp Ser Asn Gly Thr Ser Glu Ile
            515                 520                 525
```

```
Glu Glu Tyr Asp Val Val Asp Phe Asn Val Phe Phe Tyr Leu His Ala
        530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
        595                 600                 605

Ser Thr Val Asp Lys Ile Ala Asp Ile Ser Leu Ile Val Pro Tyr Val
610                 615                 620

Gly Leu Ala Leu Asn Ile Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
        675                 680                 685

Leu Ile Glu Arg Glu Ala Lys Trp Lys Glu Ile Tyr Ser Trp Ile Val
690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Leu Asn Lys Lys
        755                 760                 765

Val Ser Leu Ala Met Lys Asn Ile Glu Arg Phe Met Thr Glu Ser Ser
770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
            820                 825                 830

Val Thr Ser Thr Leu Asn Ser Ser Ile Pro Phe Glu Leu Ser Ser Tyr
        835                 840                 845

Thr Asn Asp Lys Ile Leu Ile Ile Tyr Phe Asn Arg Leu Tyr Lys Lys
850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
            900                 905                 910

Leu Ser Glu Val Asn Ile Ala Gln Asn Asn Asp Ile Ile Tyr Asn Ser
        915                 920                 925

Arg Tyr Gln Asn Phe Ser Ile Ser Phe Trp Val Arg Ile Pro Lys His
930                 935                 940
```

```
Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
            965                 970                 975

Cys Glu Ile Ile Trp Thr Leu Gln Asp Thr Ser Gly Asn Lys Glu Asn
        980                 985                 990

Leu Ile Phe Arg Tyr Glu Glu Leu Asn Arg Ile Ser Asn Tyr Ile Asn
    995                 1000                1005

Lys Trp Ile Phe Val Thr Ile Thr Asn Asn Arg Leu Gly Asn Ser
    1010                1015                1020

Arg Ile Tyr Ile Asn Gly Asn Leu Ile Val Glu Lys Ser Ile Ser
    1025                1030                1035

Asn Leu Gly Asp Ile His Val Ser Asp Asn Ile Leu Phe Lys Ile
    1040                1045                1050

Val Gly Cys Asp Asp Glu Thr Tyr Val Gly Ile Arg Tyr Phe Lys
    1055                1060                1065

Val Phe Asn Thr Glu Leu Asp Lys Thr Glu Ile Glu Thr Leu Tyr
    1070                1075                1080

Ser Asn Glu Pro Asp Pro Ser Ile Leu Lys Asn Tyr Trp Gly Asn
    1085                1090                1095

Tyr Leu Leu Tyr Asn Lys Lys Tyr Tyr Leu Phe Asn Leu Leu Arg
    1100                1105                1110

Lys Asp Lys Tyr Ile Thr Leu Asn Ser Gly Ile Leu Asn Ile Asn
    1115                1120                1125

Gln Gln Arg Gly Val Thr Glu Gly Ser Val Phe Leu Asn Tyr Lys
    1130                1135                1140

Leu Tyr Glu Gly Val Glu Val Ile Ile Arg Lys Asn Gly Pro Ile
    1145                1150                1155

Asp Ile Ser Asn Thr Asp Asn Phe Val Arg Lys Asn Asp Leu Ala
    1160                1165                1170

Tyr Ile Asn Val Val Asp Arg Gly Val Glu Tyr Arg Leu Tyr Ala
    1175                1180                1185

Asp Thr Lys Ser Glu Lys Glu Lys Ile Ile Arg Thr Ser Asn Leu
    1190                1195                1200

Asn Asp Ser Leu Gly Gln Ile Ile Val Met Asp Ser Ile Gly Asn
    1205                1210                1215

Asn Cys Thr Met Asn Phe Gln Asn Asn Asn Gly Ser Asn Ile Gly
    1220                1225                1230

Leu Leu Gly Phe His Ser Asn Asn Leu Val Ala Ser Ser Trp Tyr
    1235                1240                1245

Tyr Asn Asn Ile Arg Arg Asn Thr Ser Ser Asn Gly Cys Phe Trp
    1250                1255                1260

Ser Ser Ile Ser Lys Glu Asn Gly Trp Lys Glu
    1265                1270

<210> SEQ ID NO 13
<211> LENGTH: 1297
<212> TYPE: PRT
<213> ORGANISM: Clostridium botulinum

<400> SEQUENCE: 13

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30
```

```
Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
                100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
        130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445
```

-continued

```
Gln Cys Ile Ile Val Asn Asn Glu Asp Leu Phe Phe Ile Ala Asn Lys
    450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
            500                 505                 510
Glu Pro Phe Thr Asn Phe Asp Asp Ile Asp Ile Pro Val Tyr Ile Lys
        515                 520                 525
Gln Ser Ala Leu Lys Lys Ile Phe Val Asp Gly Asp Ser Leu Phe Glu
530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
            580                 585                 590
Ser Leu Phe Val Asn Trp Val Lys Gly Val Ile Asp Asp Phe Thr Ser
        595                 600                 605
Glu Ser Thr Gln Lys Ser Thr Ile Asp Lys Val Ser Asp Val Ser Ile
    610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
            660                 665                 670
Leu Glu Ser Tyr Val Gly Asn Lys Gly His Ile Ile Met Thr Ile Ser
        675                 680                 685
Asn Ala Leu Lys Lys Arg Asp Gln Lys Trp Thr Asp Met Tyr Gly Leu
    690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                725                 730                 735
Lys Ile Ile Glu Asp Gln Tyr Asn Arg Tyr Ser Glu Glu Asp Lys Met
            740                 745                 750
Asn Ile Asn Ile Asp Phe Asn Asp Ile Asp Phe Lys Leu Asn Gln Ser
        755                 760                 765
Ile Asn Leu Ala Ile Asn Asn Ile Asp Asp Phe Ile Asn Gln Cys Ser
    770                 775                 780
Ile Ser Tyr Leu Met Asn Arg Met Ile Pro Leu Ala Val Lys Lys Leu
785                 790                 795                 800
Lys Asp Phe Asp Asp Asn Leu Lys Arg Asp Leu Leu Glu Tyr Ile Asp
                805                 810                 815
Thr Asn Glu Leu Tyr Leu Leu Asp Glu Val Asn Ile Leu Lys Ser Lys
            820                 825                 830
Val Asn Arg His Leu Lys Asp Ser Ile Pro Phe Asp Leu Ser Leu Tyr
        835                 840                 845
Thr Lys Asp Thr Ile Leu Ile Gln Val Phe Asn Asn Tyr Ile Ser Asn
    850                 855                 860
Ile Ser Ser Asn Ala Ile Leu Ser Leu Ser Tyr Arg Gly Gly Arg Leu
```

-continued

```
865                 870                 875                 880
Ile Asp Ser Ser Gly Tyr Gly Ala Thr Met Asn Val Gly Ser Asp Val
                885                 890                 895
Ile Phe Asn Asp Ile Gly Asn Gly Gln Phe Lys Leu Asn Asn Ser Glu
                900                 905                 910
Asn Ser Asn Ile Thr Ala His Gln Ser Lys Phe Val Val Tyr Asp Ser
                915                 920                 925
Met Phe Asp Asn Phe Ser Ile Asn Phe Trp Val Arg Thr Pro Lys Tyr
        930                 935                 940
Asn Asn Asn Asp Ile Gln Thr Tyr Leu Gln Asn Glu Tyr Thr Ile Ile
945                 950                 955                 960
Ser Cys Ile Lys Asn Asp Ser Gly Trp Lys Val Ser Ile Lys Gly Asn
                965                 970                 975
Arg Ile Ile Trp Thr Leu Ile Asp Val Asn Ala Lys Ser Lys Ser Ile
                980                 985                 990
Phe Phe Glu Tyr Ser Ile Lys Asp Asn Ile Ser Asp Tyr Ile Asn Lys
                995                1000                1005
Trp Phe Ser Ile Thr Ile Thr Asn Asp Arg Leu Gly Asn Ala Asn
        1010                1015                1020
Ile Tyr Ile Asn Gly Ser Leu Lys Lys Ser Glu Lys Ile Leu Asn
        1025                1030                1035
Leu Asp Arg Ile Asn Ser Ser Asn Asp Ile Asp Phe Lys Leu Ile
        1040                1045                1050
Asn Cys Thr Asp Thr Thr Lys Phe Val Trp Ile Lys Asp Phe Asn
        1055                1060                1065
Ile Phe Gly Arg Glu Leu Asn Ala Thr Glu Val Ser Ser Leu Tyr
        1070                1075                1080
Trp Ile Gln Ser Ser Thr Asn Thr Leu Lys Asp Phe Trp Gly Asn
        1085                1090                1095
Pro Leu Arg Tyr Asp Thr Gln Tyr Tyr Leu Phe Asn Gln Gly Met
        1100                1105                1110
Gln Asn Ile Tyr Ile Lys Tyr Phe Ser Lys Ala Ser Met Gly Glu
        1115                1120                1125
Thr Ala Pro Arg Thr Asn Phe Asn Asn Ala Ala Ile Asn Tyr Gln
        1130                1135                1140
Asn Leu Tyr Leu Gly Leu Arg Phe Ile Ile Lys Lys Ala Ser Asn
        1145                1150                1155
Ser Arg Asn Ile Asn Asn Asp Asn Ile Val Arg Glu Gly Asp Tyr
        1160                1165                1170
Ile Tyr Leu Asn Ile Asp Asn Ile Ser Asp Glu Ser Tyr Arg Val
        1175                1180                1185
Tyr Val Leu Val Asn Ser Lys Glu Ile Gln Thr Gln Leu Phe Leu
        1190                1195                1200
Ala Pro Ile Asn Asp Asp Pro Thr Phe Tyr Asp Val Leu Gln Ile
        1205                1210                1215
Lys Lys Tyr Tyr Glu Lys Thr Thr Tyr Asn Cys Gln Ile Leu Cys
        1220                1225                1230
Glu Lys Asp Thr Lys Thr Phe Gly Leu Phe Gly Ile Gly Lys Phe
        1235                1240                1245
Val Lys Asp Tyr Gly Tyr Val Trp Asp Thr Tyr Asp Asn Tyr Phe
        1250                1255                1260
Cys Ile Ser Gln Trp Tyr Leu Arg Arg Ile Ser Glu Asn Ile Asn
        1265                1270                1275
```

Lys Leu Arg Leu Gly Cys Asn Trp Gln Phe Ile Pro Val Asp Glu
            1280                1285                1290

Gly Trp Thr Glu
    1295

<210> SEQ ID NO 14
<211> LENGTH: 1315
<212> TYPE: PRT
<213> ORGANISM: Clostridium tetani

<400> SEQUENCE: 14

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                325                 330                 335

Asn Gly Gln Tyr Ile Val Asn Glu Asp Lys Phe Gln Ile Leu Tyr Asn

```
                340             345             350
Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
        370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
        435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
        515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
        595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
    690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765
```

-continued

Glu Gln Ile Ala Asp Glu Ile Asn Asn Leu Lys Asn Lys Leu Glu Glu
　　 770　　　　　　　　 775　　　　　　　　 780

Lys Ala Asn Lys Ala Met Ile Asn Ile Asn Ile Phe Met Arg Glu Ser
785　　　　　　　　 790　　　　　　　　 795　　　　　　　　 800

Ser Arg Ser Phe Leu Val Asn Gln Met Ile Asn Glu Ala Lys Lys Gln
　　　　　　　　 805　　　　　　　　 810　　　　　　　　 815

Leu Leu Glu Phe Asp Thr Gln Ser Lys Asn Ile Leu Met Gln Tyr Ile
　　　　　 820　　　　　　　　 825　　　　　　　　 830

Lys Ala Asn Ser Lys Phe Ile Gly Ile Thr Glu Leu Lys Lys Leu Glu
　　　　 835　　　　　　　　 840　　　　　　　　 845

Ser Lys Ile Asn Lys Val Phe Ser Thr Pro Ile Pro Phe Ser Tyr Ser
　　 850　　　　　　　　 855　　　　　　　　 860

Lys Asn Leu Asp Cys Trp Val Asp Asn Glu Glu Asp Ile Asp Val Ile
865　　　　　　　　 870　　　　　　　　 875　　　　　　　　 880

Leu Lys Lys Ser Thr Ile Leu Asn Leu Asp Ile Asn Asn Asp Ile Ile
　　　　　　　　 885　　　　　　　　 890　　　　　　　　 895

Ser Asp Ile Ser Gly Phe Asn Ser Ser Val Ile Thr Tyr Pro Asp Ala
　　　　　 900　　　　　　　　 905　　　　　　　　 910

Gln Leu Val Pro Gly Ile Asn Gly Lys Ala Ile His Leu Val Asn Asn
　　　　 915　　　　　　　　 920　　　　　　　　 925

Glu Ser Ser Glu Val Ile Val His Lys Ala Met Asp Ile Glu Tyr Asn
　　 930　　　　　　　　 935　　　　　　　　 940

Asp Met Phe Asn Asn Phe Thr Val Ser Phe Trp Leu Arg Val Pro Lys
945　　　　　　　　 950　　　　　　　　 955　　　　　　　　 960

Val Ser Ala Ser His Leu Glu Gln Tyr Gly Thr Asn Glu Tyr Ser Ile
　　　　　　　　 965　　　　　　　　 970　　　　　　　　 975

Ile Ser Ser Met Lys Lys His Ser Leu Ser Ile Gly Ser Gly Trp Ser
　　　　　 980　　　　　　　　 985　　　　　　　　 990

Val Ser Leu Lys Gly Asn Asn Leu Ile Trp Thr Leu Lys Asp Ser Ala
　　　　 995　　　　　　　 1000　　　　　　　　 1005

Gly Glu Val Arg Gln Ile Thr Phe Arg Asp Leu Pro Asp Lys Phe
　　 1010　　　　　　　　 1015　　　　　　　　 1020

Asn Ala Tyr Leu Ala Asn Lys Trp Val Phe Ile Thr Ile Thr Asn
　　 1025　　　　　　　　 1030　　　　　　　　 1035

Asp Arg Leu Ser Ser Ala Asn Leu Tyr Ile Asn Gly Val Leu Met
　　 1040　　　　　　　　 1045　　　　　　　　 1050

Gly Ser Ala Glu Ile Thr Gly Leu Gly Ala Ile Arg Glu Asp Asn
　　 1055　　　　　　　　 1060　　　　　　　　 1065

Asn Ile Thr Leu Lys Leu Asp Arg Cys Asn Asn Asn Asn Gln Tyr
　　 1070　　　　　　　　 1075　　　　　　　　 1080

Val Ser Ile Asp Lys Phe Arg Ile Phe Cys Lys Ala Leu Asn Pro
　　 1085　　　　　　　　 1090　　　　　　　　 1095

Lys Glu Ile Glu Lys Leu Tyr Thr Ser Tyr Leu Ser Ile Thr Phe
　　 1100　　　　　　　　 1105　　　　　　　　 1110

Leu Arg Asp Phe Trp Gly Asn Pro Leu Arg Tyr Asp Thr Glu Tyr
　　 1115　　　　　　　　 1120　　　　　　　　 1125

Tyr Leu Ile Pro Val Ala Ser Ser Ser Lys Asp Val Gln Leu Lys
　　 1130　　　　　　　　 1135　　　　　　　　 1140

Asn Ile Thr Asp Tyr Met Tyr Leu Thr Asn Ala Pro Ser Tyr Thr
　　 1145　　　　　　　　 1150　　　　　　　　 1155

Asn Gly Lys Leu Asn Ile Tyr Tyr Arg Arg Leu Tyr Asn Gly Leu
　　 1160　　　　　　　　 1165　　　　　　　　 1170

```
Lys Phe Ile Ile Lys Arg Tyr Thr Pro Asn Asn Glu Ile Asp Ser
    1175            1180            1185

Phe Val Lys Ser Gly Asp Phe Ile Lys Leu Tyr Val Ser Tyr Asn
    1190            1195            1200

Asn Asn Glu His Ile Val Gly Tyr Pro Lys Asp Gly Asn Ala Phe
    1205            1210            1215

Asn Asn Leu Asp Arg Ile Leu Arg Val Gly Tyr Asn Ala Pro Gly
    1220            1225            1230

Ile Pro Leu Tyr Lys Lys Met Glu Ala Val Lys Leu Arg Asp Leu
    1235            1240            1245

Lys Thr Tyr Ser Val Gln Leu Lys Leu Tyr Asp Asp Lys Asn Ala
    1250            1255            1260

Ser Leu Gly Leu Val Gly Thr His Asn Gly Gln Ile Gly Asn Asp
    1265            1270            1275

Pro Asn Arg Asp Ile Leu Ile Ala Ser Asn Trp Tyr Phe Asn His
    1280            1285            1290

Leu Lys Asp Lys Ile Leu Gly Cys Asp Trp Tyr Phe Val Pro Thr
    1295            1300            1305

Asp Glu Gly Trp Thr Asn Asp
    1310            1315

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5
```